United States Patent [19]

Ong et al.

[11] 4,198,418

[45] Apr. 15, 1980

[54] SPIRO[DIBENZ(B,F)OXEPIN-PIPERIDINE]S

[75] Inventors: Helen H. Ong, Whippany; James A. Profitt, Somerville, both of N.J.

[73] Assignee: American Hoechst Corporation, Bridgewater, N.J.

[21] Appl. No.: 2,348

[22] Filed: Jan. 10, 1979

[51] Int. Cl.$^2$ .................. C07D 491/10; A61K 31/55; A61K 31/44
[52] U.S. Cl. .................................... 424/267; 546/17; 546/215; 546/228; 546/226; 260/465 F; 260/465 G; 562/471; 562/472; 568/638; 568/639

[58] Field of Search .......................... 546/17; 424/267

[56] References Cited

U.S. PATENT DOCUMENTS 4,001,419   1/1977   Galt et al. ............................. 546/17

*Primary Examiner*—Henry R. Jiles
*Assistant Examiner*—Robert T. Bond
*Attorney, Agent, or Firm*—Curtis, Morris & Safford

[57] ABSTRACT

Novel spiro[dibenz(b,f)oxepin-piperidine]s and methods of preparing same are described. These compounds are useful as analgetics, tranquilizers and anticonvulsants.

54 Claims, No Drawings

SPIRO[DIBENZ(B,F)OXEPIN-PIPERIDINE]S

This invention relates to novel spiro[dibenz(b,f)-oxepin-piperidine]s, and to pharmaceutically acceptable acid addition salts thereof, which are useful analgetics, tranquilizers and anticonvulsants, to methods of treatment with pharmaceutically effective amounts thereof and to pharmaceutical compositions containing such a compound as an essential active ingredient. The compounds of the invention have the formula

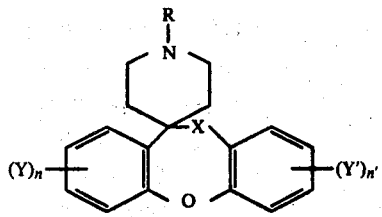

in which R is hydrogen, alkyl, alkenyl, alkynyl, hydroxyalkyl, cycloalkylalkyl, unsubstituted or substituted phenylalkyl, unsubstituted or substituted phenoxyalkyl, alkanoyl, unsubstituted or substituted benzoylalkyl, cyano or ethylene glycol ketal of the formula

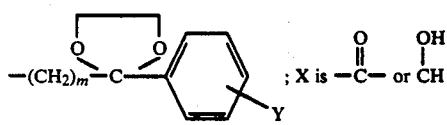

when R is as defined previously,

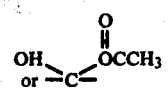

when R is alkanoyl, methyl or cyano; Y and Y' are the same or different and each can be hydrogen, chlorine, fluorine, bromine, methoxy, methylthio or trifluoromethyl; n and n' are the same or different and each can be an integer from 1 to 2, inclusive; and m is an integer from 1 to 4, inclusive.

In the above definitions and throughout this application, the following have the assigned significance, unless otherwise indicated:

"alkyl" contains between 1 and 6, inclusive, carbon atoms and can be straight or branched chain;

"alkenyl," "alkynyl," or "alkanoyl," each may contain between 2 and 6, inclusive, carbon atoms and can be straight or branched chain;

"cycloalkyl" contains between 3 and 7, inclusive, carbon atoms; and

"substituted" means the phenyl of the particular group is substituted by one or more of the following:

nitro, amino, chlorine, fluorine, bromine, methoxy, loweralkyl or trifluoromethyl.

Acids useful for preparing the pharmaceutically acceptable acid salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic.

To the best of our knowledge, the compounds of the present invention have not heretofore been described or suggested. Galt et al. in U.S. Pat. No. 4,001,419 describes, as analgetics, 1'-substituted xanthene 9-spiro-4'-piperidine derivatives, depicted by the formula

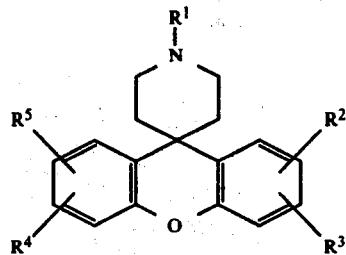

in which $R^1$ stands for a hydrogen atom, alkyl radical of 1 to 10 carbon atoms; an alkenyl radical of 3 to 10 carbon atoms, a haloalkenyl radical of 3 to 6 carbon atoms, a cycloalkylalkyl radical of 4 to 7 carbon atoms, optionally substituted in the cycloalkyl nucleus by an aryl radical of 6 to 10 carbon atoms or by one or two alkyl radicals of 1 to 3 carbon atoms, a phenyl radical, an arylalkyl radical of 7 to 10 carbon atoms, optionally substituted in the aryl nucleus by one to three halogen atoms or alkyl radicals of 1 to 3 carbon atoms, hydroxyalkyl radical of 2 to 5 carbon atoms, a dialkylaminoalkyl radical of 4 to 8 carbon atoms, a carbamoylalkyl radical of 2 to 8 carbon atoms, an alkylcarbamoylalkyl radical of 3 to 8 carbon atoms, or an alkanoylalkyl radical of 3 to 8 carbon atoms; $R^2$, $R^3$, $R^4$ and $R^5$ are the same or different and each can be hydrogen atoms, halogen atoms, alkyl radicals of 1 to 5 carbon atoms, haloalkyl radicals of 1 to 5 carbon atoms, alkoxy radicals of 1 to 5 carbon atoms, alkylthio radicals of 1 to 5 carbon atoms, hydroxy radicals, thiol radicals, alkanoylamino radicals of 1 to 5 carbon atoms, alkanoyloxy radicals of 1 to 5 carbon atoms, aroyloxy radicals of 7 to 10 carbon atoms, optionally substituted in the aryl nucleus by one to three halogen atoms or alkyl radicals of 1 to 3 carbon atoms, arylalkenoyloxy radicals of 9 to 12 carbon atoms, hydroxyalkyl radicals of 1 to 5 carbon atoms, alkylsulphinyl radicals of 1 to 5 carbon atoms or alkanesulphonylyl radicals of 1 to 5 carbon atoms; and the pharmaceutically acceptable acid addition salts thereof.

Also, Gerecke et al., in French Pat. No. 824066 disclose, as tranquilizers, tricyclic compounds depicted by the formula

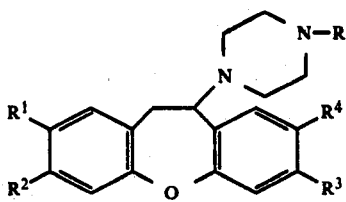

in which R represents a loweralkyl, loweralkenylalkyl or loweralkynylalkyl group that may be substituted by a cyano, hydroxy or alkanoyloxy group in the case in which they do not represent methyl groups or in which R represents a group of the general formula

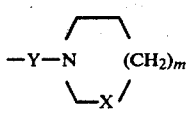

in which X represents an oxygen or a sulfur atom, an imino group, a lower alkylimino group or a methylene group; Y represents an ethylene or propylene group possibly substituted by a loweralkyl group; and m equals 0 or 1; further, one of the substituents $R_1$ and $R_2$ represents a hydrogen atom and the other a loweralkyl, loweralkoxy, loweralkylthio group, a halogen, a trifluoromethyl or a hydroxy group and one of the substituents $R_3$ and $R_4$ represents hydrogen and the other a hydrogen atom, a loweralkyl, loweralkoxy, loweralkylthio group, a halogen or a trifluoromethyl or hydroxy group, and salts of these compounds.

However, neither of these two disclosures suggests the presently disclosed compounds.

The compounds of the invention can be prepared according to one or more of the following methods in which R, X, Y, Y' and Z are as defined above, unless otherwise indicated.

METHOD A

1. A 2-phenoxyphenylacetonitrile depicted by the formula

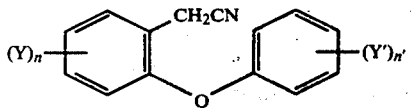

is subjected to bis-alkylation with mechlorethamine.hydrochloride in the presence of a strong base (as acid scavenger) at a temperature ranging from about ambient to about 85° C. to provide the corresponding 4-cyano-1-methyl-4-(2-phenoxyphenyl)piperidine depicted by the formula

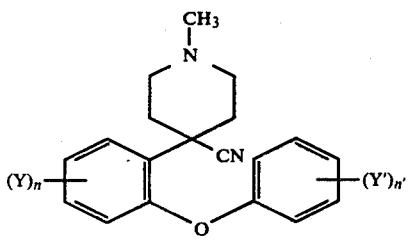

Preferred methods include the use of dimethylformamide or dimethylsulfoxide as the solvent and sodium hydride as the acid scavenger.

2. A compound of formula II is treated in accordance with the first step of the von Braun reaction to provide the corresponding 1,4-dicyano-4-(2-phenoxyphenyl)-piperidine depicted by the formula

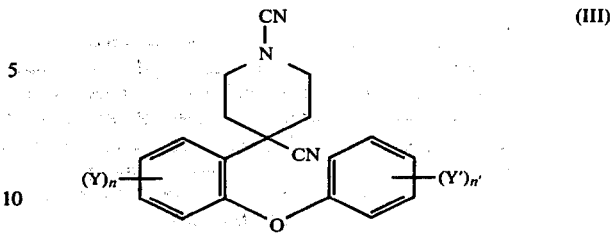

In this reaction cyanogen bromide is utilized to replace the N-methyl. Also, a solvent such as chloroform or methylene dichloride, a mild base acting as acid scavenger such as potassium carbonate and a reaction temperature ranging from about ambient to reflux of the reaction mixture constitute the reaction conditions.

3. A compound of formula III is subjected to acid hydrolysis to provide the corresponding 4-(2-phenoxyphenyl)piperidine-4-carboxylic acid depicted by the formula

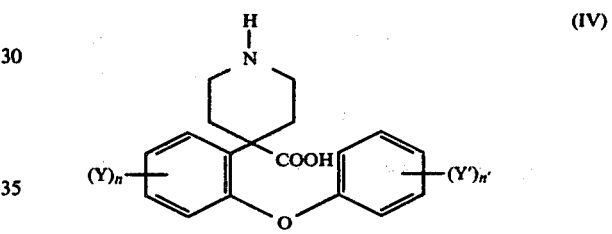

A preferred method utilizes concentrated (48%) hydrobromic acid under reflux conditions.

4. A compound of formula IV is acylated in the presence of a basic solvent or an acid scavenger to provide the corresponding 1-alkanoyl-4-(2-phenoxyphenyl)-piperidine-4-carboxylic acid depicted by the formula

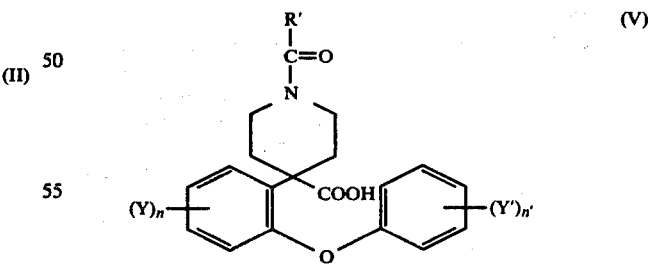

in which R' is alkyl. A preferred solvent is pyridine and an acid scavenger is potassium carbonate. An appropriate alkanoyl halide, e.g. acetyl chloride, or an anhydride, e.g. acetic anhydride can be the acylating agent.

5. A compound of formula V is carefully subjected to reaction with a thionyl halide to provide the corresponding acid halide depicted by the formula

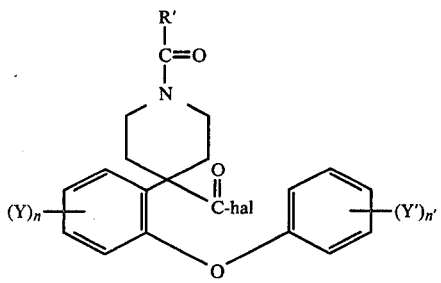

A preferred method utilizes thionyl chloride with the reaction carried out by heating on a steam bath for about 5 minutes.

6. A compound of formula VI is cycliacylated to provide the corresponding 10,11-dihydro-1'-alkanoyl-11-oxospiro[dibenz[b,f]oxepin-10,4'-piperidine], a compound of the invention, depicted by the formula

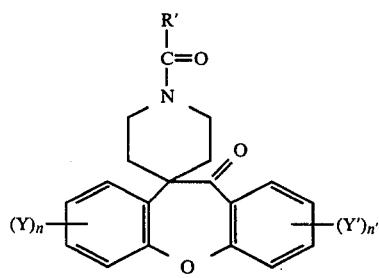

Said cycliacylation can be carried out via the acid chloride under modified Friedel-Crafts conditions with a Lewis acid catalyst such as aluminum chloride or ferric chloride. A preferred solvent is methylene chloride. Reaction temperature may range from about 15° C. to about 150° C. A preferred method utilizes the acid chloride formula VI, aluminum chloride, methylene dichloride and reflux conditions.

METHOD B

1. A compound of formula II is subjected to acid hydrolysis according to Method A (3) to provide the corresponding carboxylic acid depicted by the formula

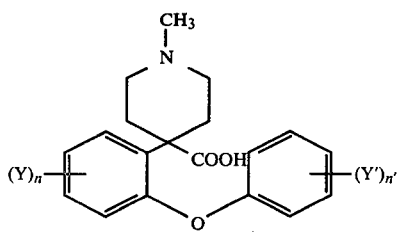

2. A compound of formula VIII is cycliacylated to provide the corresponding 10,11-dihydro-1'-methyl-11-oxospiro[dibenz(b,f)oxepin-10,4'-piperidine], a compound of the invention depicted by the formula

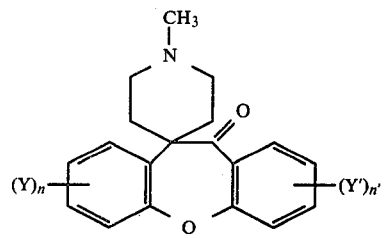

A preferred method utilizes a dehydrating medium such as polyphosphoric acid and a reaction temperature of about 95°–115° C. Alternatively, the procedure of Method A (6) may be utilized.

METHOD C

A compound of formula VII is subjected to acid hydrolysis to provide the corresponding N-unsubstituted compound of the invention depicted by the formula 3 N hydrochloric acid under reflux conditions constitutes a preferred method of carrying out this hydrolysis.

METHOD D

1. A compound of formula IX or XIII below is treated in accordance with Method A (2) to provide the corresponding N-cyano compound of the invention depicted by the formula 2. A compound of formula XI, is subjected to hydrolysis in accordance with the second step of the von Braun reaction to provide the corresponding N-unsubstituted compound of the invention depicted in formula X, above. In this procedure, a mixture of 3 N hydrochloric and glacial acetic acid (2:1) and temperatures ranging from about 75° to 150° C. are utilized.

METHOD E

A compound of formulas VII, IX, or XI, above, can be acylated under Friedel Craft conditions, as described in Method A (6) to provide the corresponding 11-alkanoyloxy-11-hydroxy compound of the invention depicted by the formula

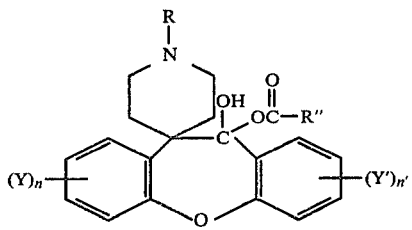

in which R is

CH₃, or CN; R' and R" are the same or different and each is alkyl.

METHOD F

A compound of formula VII, IX, X or XI, above, is reduced to provide the corresponding 11-hydroxy compound of the invention depicted by formula

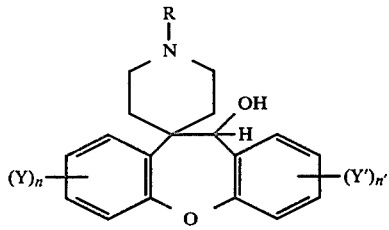

in which R is alkyl or H. A preferred method utilizes lithium aluminum hydride as the reducing agent, tetrahydrofuran as a solvent and a reaction temperature ranging from ambient to reflux of the reaction mixture.

METHOD G

A compound of formula X, or XIII (R=H) is alkylated or acylated with an appropriate alkylating agent by any convenient method known to the art to provide the corresponding N-substituted compound of the invention of the formula (XIV)

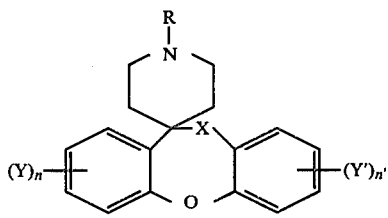

in which R is alkyl, hydroxyalkyl, alkynyl, alkenyl, phenylalkyl, phenoxyalkyl, cycloalkylalkyl, alkanoyl or benzoylalkyl, and X is

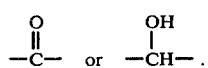

Preferred methods utilize an alkylating agent of the formula R-halide with the alkylation carried out in a solvent such as dimethylformamide, an acid scavenger such as sodium bicarbonate or potassium carbonate, a reaction initiator such as potassium iodide and a reaction temperature ranging from about ambient to reflux of the reaction mixture.

METHOD H

1. A compound of formula X, or XIII (R=H) is treated with a chloro ethylene glycol ketal of the formula

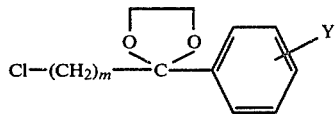

according to conditions consistent with those of Method G to provide the corresponding compound of the invention in which R is benzoylalkyl ethylene ketal.

2. An ethylene ketal compound of the invention is subjected to acid hydrolysis to provide the corresponding compound of the invention in which R is benzoyl-loweralkyl

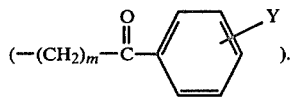

A preferred method utilizes 3 N hydrochloric acid in ethanol as the agent effecting hydrolysis.

METHOD I

A compound of formula X or XIII (R=H) is treated according to the conditions of the Eschweiler-Clarke reaction to provide the corresponding compound of the invention in which R is methyl. This method is carried out by reacting, under reflux conditions, with formic acid and formaldehyde.

In each of the above methods optimum conditions depend upon starting materials, solvents, catalysts and other reaction components. This will become more apparent in the examples given below.

Starting materials conforming to formula I are either commercially available or can be prepared by routine methods according to the following sequence of reactions:

1.

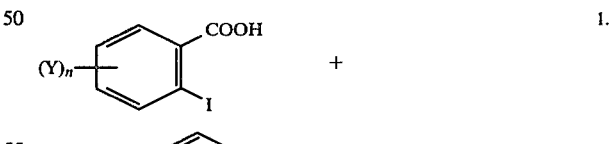

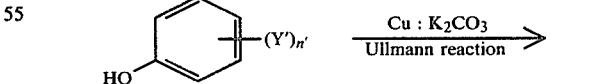

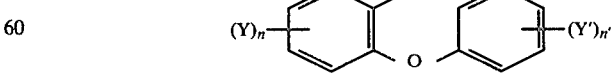

2.

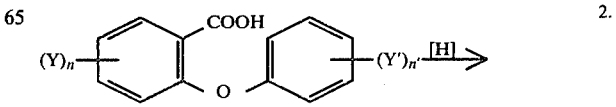

-continued

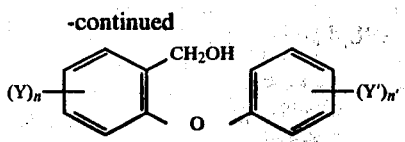

reduction with sodium bis (2-methoxyethyl)aluminum hydride (VITRIDE®)

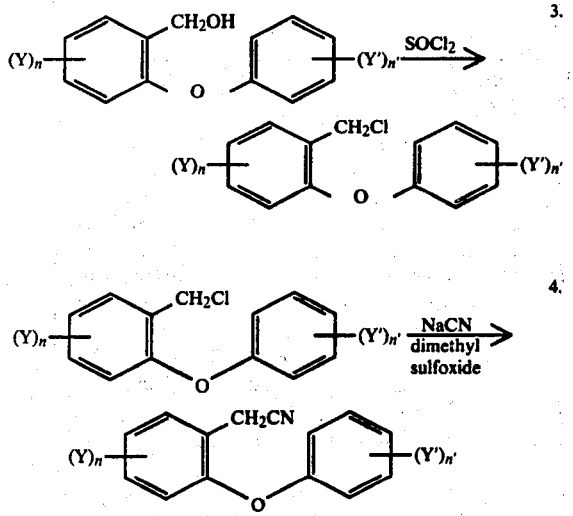

The compounds of the present invention are useful as analgetics due to their ability to alleviate pain in mammals, as demonstrated in the phenyl-α-quinone writhing assay in mice, a standard assay for analgesia [Proc. Soc. Exptl. Biol. Med., 95, 729 (1957)]. Tabulated below are the percentages of inhibition of writhing accomplished with various dosages of representative compounds of the invention

| Compound | Dose mg/kg | % Inhibition |
|---|---|---|
| 2-chloro-10,11-dihydro-1'-methyl-11-oxospiro[dibenz(b,f)oxepin-10,4'-piperidine] . HBr | 3.6 (s.c.)* 5.2 (p.o.)** | 50 50 |
| 2-chloro-10-,11-dihydro-11-oxospiro-[dibenz(b,f)oxepin-10,4'-piperidine] . HBr | 3.6 (s.c.) 7.7 (p.o.) | 50 50 |
| 10,11-dihydro-11-oxo-1'-phenylethyl-spiro[dibenz(b,f)oxepin-10,4'-piperidine]- . HBr | 25 | 67 |
| 2-chloro-10,11-dihydro-1'-ethyl-11-oxo-spiro[dibenz(b,f)oxepin-10,4'-piperidine]- . HBr | 25 | 67 |

*s.c. means subcutaneous administration
**p.o. means oral administration

For comparison, aspirin and propoxyphene, known analgesic agents, effect a 34% and 50% inhibition at a dose of 60 mg/kg and 28 mg/kg, respectively. These data illustrate that the compounds of this invention are useful for alleviating pain in mammals when administered in amounts ranging from about 0.1 to about 100 mg/kg of body weight per day.

Compounds of the present invention are also useful as tranquilizers as demonstrated by their ability to inhibit foot shock-induced rage [Arch. Int. Pharmacodynam. et de Therap., 142, 30 (1963)]. For example, at a oral dose of 20 mg/kg 10,11-dihydro-1'-[3-(4-fluorobenzoyl)propyl]-11-oxospiro-[dibenz(b,f)oxepin-10,4'-piperidine].HBr and 10,11-dihydro-11-oxo-1'-(2-propynyl)spiro[dibenz(b,f)oxepin-10,4'-piperidine].HBr effect a 100% and 50%, respectively, of mice are protected from foot-shock-induced rages. This tranquilizing utility is also shown by the ability of compounds of the invention to antagonize the toxicity of amphetamine in aggregated situations in mice [J. Pharmacol. Exp. Therap., 87, 214 (1946)]. For example, a 50 mg/kg dose of 2-chloro-10,11-dihydro-11-oxospiro[dibenz(b,f)-oxepin-10,4'-piperidine].HBr antagonizes amphetamine toxicity in 50% of mice. These data illustrate that compounds of this invention are useful as tranquilizers in mammals when administered in amounts ranging from about 0.5 to about 100 mg/kg of body weight per day.

Compounds of the present invention are further useful as anticonvulsant agents for mammals, as determined by the method of Woodbury, L. A. and Davenport, V. D. [Arch., Int. Pharmacodynam, 92, pp 97–107 (1952)]. For example, the intraperitoneal dose of 19.4 mg/kg of body weight of 2-chloro-10,11-dihydro-1'-methyl-11-oxospiro(b,f)oxepin-10,4'-piperidine].HBr produces a 50% protection from the effect of supramaximal electro shock. Similar effects are produced by the intraperitoneal doses of 27.1 and 30–50 mg/kg of 2-chloro-1'-cyclopropylmethyl-10,11-dihydro-11-oxospiro-[dibenz(b,f)oxepin-10,4'-piperidine].HBr and 10,11-dihydro-1'-methyl-11-oxospiro[dibenz(b,f)oxepin-10,4'-piperidine].HBr, respectively. These data illustrates that compounds of this invention are useful in treating convulsions in mammals when administered in amounts ranging from about 0.5 to 100 mg/kg of body weight per day.

Compounds of this invention include:
8-chloro-10,11-dihydro-2-methoxy-1'-methyl-11-oxospiro[dibenz(b,f)oxepin-10,4'-piperidine],
3-bromo-10,11-dihydro-7-methylthio-1'-methyl-11-oxospiro[dibenz(b,f)oxepin-10,4'-piperidine],
10,11-dihydro-3-methoxy-1'-methyl-11-oxo-8-trifluoromethylspiro[dibenz(b,f)oxepin-10,4'-piperidine],
10,11-dihydro-9-methoxy-1'-methyl-2-methyl-11-oxospiro-[dibenz(b,f)oxepin-10,4'-piperidine],
10,11-dihydro-1'-methyl-8-methyl-11-oxo-2-trifluoromethylspiro[dibenz(b,f)oxepin-10,4'-piperidine],
2-bromo-7-chloro-10,11-dihydro-1'-methyl-11-oxospiro[dibenz(b,f)oxepin-10,4'-piperidine],
10,11-dihydro-2,8-dimethoxy-1'-methyl-11-oxospiro[-dibenz-(b,f)oxepin-10,4'-piperidine],
10,11-dihydro-1'-methyl-2-methylthio-11-oxo-7-trifluoromethylspiro[dibenz(b,f)oxepin-10,4'-piperidine],
2-fluoro-1'-[2-(p-fluorobenzoyl)ethyl]-10,11-dihydro-11-oxospiro[dibenz(b,f)oxepin-1,4'-piperidine],
2-chloro-1'-[2-(p-fluorobenzoyl)ethyl]-10,11-dihydro-11-oxospiro[dibenz(b,f)oxepin-1,4'-piperidine],
1'-(4-benzoylbutyl)-10,11-dihydro-11-oxospiro[-dibenz(b,f)-oxepin-1,4'-piperidine],
1'-(4-benzoylbutyl)-2-chloro-10,11-dihydro-11-oxospiro[dibenz(b,f)oxepin-1,4'-piperidine],
1'-(4-benzoylbutyl)-2-fluoro-10,11-dihydro-11-oxospiro[dibenz(b,f)oxepin-1,4'-piperidine],
2-fluoro-10,11-dihydro-7,8-dimethoxy-1'-methyl-11-oxospiro[dibenz(b,f)oxepin-1,4'-piperidine],
2,3-dichloro-10,11-dihydro-1'-methyl-7-methylthio-11-oxospiro[dibenz(b,f)oxepin-1,4'-piperidine],
8-chloro-2,3-difluoro-10,11-dihydro-1'-methyl-11-oxospiro[dibenz(b,f)oxepin-1,4'-piperidine], and 2-chloro-7,8-difluoro-10,11-dihydro-1'-methyl-11-oxospiro[dibenz(b,f)oxepin-1,4'-piperidine].

Effective quantities of the compounds of the invention may be administered to a patient by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0-300 milligrams of active compound.

The tablets, pills, capsules, troches, and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent, and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied to be between 0.5 and about 50% of the weight thereof. The amount of active compounds in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylenediamine tetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

EXAMPLE 1 a.

2.6 g of 99% sodium hydride are added portionwise to a solution of 4.4 g of 2-phenoxyphenylacetonitrile in 50 ml of dimethylformamide. The resulting reddish brown mixture is stirred for 30 minutes before adding dropwise a solution of 4.0 g of mechloroethamine hydrochloride in 50 ml of dimethylformamide, maintaining gas evolution at a slow rate. After total addition, the mixture is stirred at 80°-85° C. for 15 hours. Thereafter, 100 g of ice are added before the mixture is extracted thrice with ether. The combined ether extracts are dried over potassium carbonate and then the solvent is removed under vacuum leaving a brownish oil. The oil is dissolved in a small amount of ether and passed through, with additional ether, an alumina column which is packed in ether. The filtered solution is concentrated leaving a heavy oil. The oil is converted to its hydrochloride which is recrystallized from an acetone-ether mixture, leaving shiny prisms, mp. 242°-244° C., of 4-cyano-1-methyl-4-(2-phenoxyphenyl)piperidine hydrochloride.

b.

A solution of 2.6 g of 4-cyano-1-methyl-4-(2-phenoxyphenyl)piperidine, free base of a, in 22 ml of chloroform is added rapidly to a stirred mixture of 1.5 g of cyanogen bromide and 6 g of potassium carbonate in 30 ml of chloroform. The reaction mixture is stirred at reflux for 16 hours and then filtered. The filtrate is concentrated under vacuum, leaving an oily residue. The residue is dissolved in a few mls of methyl alcohol to decompose any unreacted cyanogen bromide. Thereafter, the methyl alcohol is evaporated off, leaving a pale yellowish residue which crystallizes upon cooling. The resulting solid is recrystallized from acetone to give rhombic crystals, mp. 100°-101° C., of 1,4-dicyano-4-(2-phenoxyphenyl)-piperidine.

c.

A suspension of 8 g of 1,4-dicyano-4-(2-phenoxyphenyl)piperidine in 120 ml of 48% hydrobromic acid is stirred at reflux for 16 hours. Thereafter, any excess acid is removed by distillation under vacuum, leaving a glassy residue. The residue is dissolved in 100 ml of water. The solution becomes cloudy, crystals begin to deposit and the cloudy mixture is maintained at 0° C. for 16 hours, effecting complete crystallization. The crystals are collected and then recrystallized from an ethyl alcohol-acetone-ether mixture to provide tan-colored prisms, mp 247°-249° C., of 4-(2-phenoxyphenyl)piperidine-4-carboxylic acid hydrobromide.

d.

A mixture of 8 g of 4-(2-phenoxyphenyl)piperidine-4-carboxylic acid hydrobromide and 10 ml of acetic anhydride in 50 ml of pyridine is refluxed for 4 hours. Thereafter, any excess pyridine is removed by distillation under vacuum and the residue is triturated in 100 ml of 1 N hydrochloric acid before being extracted thrice with chloroform. The combined chloroform extracts are successively washed well with water, dried and concentrated under vacuum, leaving a solid residue. The residue is recrystallized from boiling acetone to provide small prisms, mp 195°–197.5° C., of 1-acetyl-4-(2-phenoxyphenyl)-piperidine-4-carboxylic acid.

e.

A suspension of 3.4 g of 1-acetyl-4-(2-phenoxyphenyl)piperidine-4-carboxylic acid in 5 ml of freshly distilled thionyl chloride is warmed on a steam bath for 5 minutes to effect a clear solution. Any excess thionyl chloride is removed at 50° C. under reduced pressure leaving a yellowish solid mass. The mass is recrystallized five times from a benzene-cyclohexane mixture to provide the product, mp 106°–108° C., of 1-acetyl-4-(2-phenoxyphenyl)piperidine-4-carbonyl chloride.

f.

A solution of 14 g of 1-acetyl-4-(2-phenoxyphenyl)-piperidine-4-carbonyl chloride in 500 ml of methylene chloride is slowly added with stirring to 7.5 g of aluminum chloride. After total addition, the reaction mixture is refluxed for 2 hours, effecting a color change from greenish to light tan. Thereafter, ice is added before extracting thrice with chloroform. The combined chloroform extracts are successively washed with dilute alkali, washed with water, dried and the solvent is removed under vacuum, leaving an oily residue which solidifies on standing. The solid is recrystallized from a benzene-hexane mixture to provide colorless prisms, mp 171°–172° C., of 10,11-dihydro-1'-acetyl-11-oxospiro[dibenz(b,f)oxepin-10,4'-piperidine].

Analysis: Calculated for $C_{20}H_{19}NO_3$: 74.73%C; 5.96%H; 4.35%N. Found: 74.93%C; 6.02%H; 4.43%N.

EXAMPLE 2 a.

14.4 g of 97% sodium hydride are added in small portions while stirring to a mixture of 27.6 g of 2-(4-chlorophenoxy)benzyl cyanide in 300 ml of dimethylformamide. After total addition, the mixture is stirred at ambient temperature for 45 minutes prior to adding, dropwise, 20.2 g of 98% mechlorethamine hydrochloride in 200 ml of dimethylformamide. Thereafter, the reaction mixture is stirred at 100° C. for 17 hours and permitted to cool. The cooled mixture is poured into 1000 g of ice and then stirred. The aqueous mixture is extracted five times with 250 ml portions of ether. The combined ether extracts are extracted with 2 N hydrochloric acid and the combined acidic extracts are basified with a concentrated ammonium hydroxide solution, providing an oil. The oil is extracted with three 250 ml portions of ether and the combined ether extracts are dried, providing a dark crystalline material. The solid is chromatographed on an alumina column, ether eluant, to provide a white crystalline product, mp 95°–97° C., of 1-methyl-4-cyano-4-[2-(4-chlorophenoxyphenyl)]piperidine.

b.

A solution of 1.1 g of 1-methyl-4-cyano-4-[2-(4-chlorophenoxyphenyl)]piperidine in 25 ml of 48% hydrobromic acid is stirred at 130° C. for 16 hours. Thereafter, the reaction solution is diluted with 175 ml of water and rotary evaporated under reduced pressure at 85° C. to remove any excess acid. The resulting glassy solid is dissolved in water and passed through a column of Bio-Rad AG 50W-X8 cation exchange resin, 1.5 N ammonium hydroxide eluant, to provide a white powder, mp 320° C., of 4-[2-(4-chlorophenoxyphenyl)]-1-methylpiperidine-4-carboxylic acid.

Analysis: Calculated for $C_{19}H_{20}ClNO_3$: 65.99%C; 5.83%H; 4.05%N; 10.25%Cl. Found: 65.80%C; 5.68%H; 3.93%N; 10.50%Cl.

c.

A mixture of 4.4 g of 4-[2-(4-chlorophenoxyphenyl)]-1-methylpiperidine-4-carboxylic acid and 40 ml of polyphosphoric acid, under nitrogen, is stirred at 100°–110° C. for 2 hours. Thereafter, the reaction is cooled to 0° C. before 10 ml of ice and 70 ml of water are added. The mixture is made alkaline with concentrated ammonium hydroxide solution and is extracted with four 100 ml portions of ether. The combined ether extracts are washed sequentially with 100 ml of water, 100 ml of a 10% sodium hydroxide solution and 50 ml of a saturated sodium chloride solution. The washed solution is dried, effecting an oil. The oil is chromatographed on a silica gel 60 column, a methyl alcohol-chloroform (1:6) mixture eluant providing a purer oil which is converted in ether to its hydrobromide salt. The salt is recrystallized from a methyl alcohol-ether mixture to provide a white solid, mp 304°–306° C., of 2-chloro-10,11-dihydro-1'-methyl-11-oxospiro[dibenz(b,f)oxepin-10,4'-piperidine]-hydrobromide.

Analysis: Calculated for $C_{19}H_{18}ClNO_2 \cdot HBr$: 55.87%C; 4.69%H; 3.43%N; 19.57%Br. Found: 55.45%C; 4.97%H; 3.25%N; 19.66%Br.

EXAMPLE 3

A suspension of 2.0 g of 10,11-dihydro-1'-acetyl-11-oxospiro[dibenz(b,f)oxepin-1,4'-piperidine], Example 1, in 15 ml of 3 N hydrochloric acid is stirred at reflux for 3 hours. The resulting clear solution is diluted with cold water and then extracted with ethyl acetate. The acidic, aqueous, solution is basified with potassium carbonate freeing an amine which is dissolved in ether. The ether solution is successively dried and concentrated under vacuum leaving a pale yellowish oil which is converted, in ether, to its hydrobromic acid salt. The salt is recrystallized from a methyl alcohol-acetone-ether mixture to give needles, mp 280°–282° C., of 10,11-dihydro-11-oxospiro[dibenz-(b,f)oxepin-10,4'-piperidine]hydrobromide.

Analysis: Calculated for $C_{18}H_{17}NO_2 \cdot HBr$: 60.02%C; 5.03%H; 3.88%N; 22.18%Br. Found: 60.02%C; 5.10%H; 3.77%N; 22.31%Br.

EXAMPLE 4

A mixture of 3.5 g of 2-chloro-10,11-dihydro-1'-methyl-11-oxospiro[dibenz(b,f)oxepin-10,4'-piperidine], free base of Example 2, with 7.1 g of potassium carbonate and 1.8 g of cyanogen bromide in 45 ml of methylene chloride is refluxed for 2 hours. Thereafter, the mixture is filtered and the filtrate rotary evaporated leaving a solid. The solid is dissolved in 30 ml of methyl alcohol and the solution is refluxed for 10 minutes and then rotary evaporated again leaving a solid. This solid is chromatographed on 50 g of silica gel 60 with ether leaving a non-crystalline solid which is dissolved in chloroform. The chloroform solution is rotary evaporated leaving a crisp foam which can be broken easily into a white powder. The powder is recrystallized from acetone providing the product, mp 141.5°–143.0° C., of 2-chloro-1'-cyano-10,11-dihydro-11-oxospiro[dibenz(b,f)oxepin-10,4'-piperidine].

Analysis: Calculated for $C_{19}H_{15}ClN_2O_2$: 67.36%C; 4.46%H; 8.27%N. Found: 67.43%C; 4.65%H; 8.19%N.

EXAMPLE 5

A homogeneous solution of 1.8 g of 2-chloro-1'-cyano-10,11-dihydro-11-oxospiro[dibenz(b,f)oxepin-10,4'-piperidine], Example 4, in 20 ml of 3 N hydrochloric acid and 10 ml of glacial acetic acid is stirred at 110°–120° C. for 16 hours and then the solution is permitted to cool to ambient temperature. Thereafter, the solution is diluted with 50 ml of water and then is rotary evaporated at 80° C. until 50 ml of water is removed and the dilution and evaporation process is repeated. The residue is diluted with 200 ml of water and the diluted solution is successively cooled in an ice bath, basified to pH 9 with a small amount of 58% ammonium hydroxide and extracted thrice with 80 ml portions of ether. The combined ether extracts are sequentially washed twice with two 80 ml portions of water and one 40 ml portion of saturated sodium chloride and then dried over magnesium sulfate and finally evaporated to dryness leaving an oil. The oil is dissolved in ether where it is converted to its hydrobromic acid salt. The salt is recrystallized from acetone to provide crystals of 2-chloro-10,11-dihydro-11-oxospiro[dibenz(b,f)oxepin-10,4'-piperidine]hydrobromide which lose their regular shape upon heating above 125° C. and the resulting glass melts at 223°–225° C.

Analysis: Calculated for $C_{18}H_{16}ClNO_2 \cdot HBr$: 54.77%C; 4.34%H; 3.55%N; Total Hal 29.2 Found: 54.69%C; 4.47%H; 3.39%N; Total Hal 29.0

EXAMPLE 6

A solution of 0.4 g of acetyl chloride dissolved in methylene chloride is added over a 1–2 minute span to a stirred mixture of 1.0 g of 10,11-dihydro-1'-acetyl-11-oxospiro[dibenz(b,f)oxepin-10,4'-piperidine], Example 1, and 0.94 g of aluminum chloride in 20 ml of methylene chloride. After total addition, the reaction mixture is stirred at ambient temperature for 16 hours and then decomposed with ice-water. The organic phase is successively extracted thrice with an ethyl acetate-ether (1:1) mixture, sequentially washed with sodium bicarbonate solution, water and brine, dried and concentrated under vacuum, leaving a yellowish oil which crystallizes upon scratching. The resulting solid is recrystallized from an acetone-hexane mixture to provide prisms, mp 193°–196° C., of 10,11-dihydro-11-acetoxy-1'-acetyl-11-hydroxyspiro[dibenz(b,f)oxepin-10,4'-piperidine].

Analysis: Calculated for $C_{22}H_{23}NO_5$: 69.29%C; 6.08%H; 3.65%N. Found: 69.28%C; 6.15%H; 3.58%N.

EXAMPLE 7

A solution of 2.4 g of 10,11-dihydro-11-oxospiro[dibenz(b,f)oxepin-10,4'-piperidine], free base of Example 3, in 20 ml of tetrahydrofuran is added dropwise to a refluxing slurry of 1.5 g of lithium aluminum hydride in 20 ml of tetrahydrofuran. After total addition, stirring is continued at reflux for an additional 4 hours and then at ambient temperature for 16 hours. Thereafter, the reaction mixture is decomposed by adding sequentially 1.7 ml of water with 1.7 ml of 15% sodium hydroxide and 5.2 ml of water. The diluted mixture is filtered and the filtrate is concentrated under vacuum to provide a solid residue. The residue is recrystallized from boiling acetone to provide colorless prisms, mp 202°–203.5° C., of 10,11-dihydro-11-hydroxyspiro[dibenz(b,f)oxepin-10,4'-piperidine].

Analysis: Calculated for $C_{18}H_{19}NO_2$: 76.86%C; 6.80%H; 4.97%N. Found: 76.77%C; 6.83%H; 4.96%N.

EXAMPLE 8

A mixture of 1.1 g of 10,11-dihydro-11-oxospiro[dibenz(b,f)oxepin-10,4'-piperidine], free base of Example 3, in 8 ml of formic acid is refluxed for 2 hours before adding 7.2 ml of formalin (38% formaldehyde in water). After the addition, stirring and refluxing continues for 16 hours. Thereafter, the reaction mixture is removed under reduced pressure and the residue is basified with dilute alkali. An oil separates and is extracted into ether. The combined ether extracts are dried and then evaporated under vacuum, providing a colorless oil. The oil is dissolved in ether, where it is converted to its hydrobromic acid salt which is recrystallized from a methyl alcohol-ether mixture to provide microgranules, mp>290° C., of 10,11-dihydro-1'-methyl-11-oxospiro[dibenz(b,f)oxepin-10,4'-piperidine]hydrobromide.

Analysis: Calculated for $C_{19}H_{19}NO_2 \cdot HBr$: 60.96%C; 5.38%H; 3.74%N; 21.35%Br. Found: 61.14%C; 5.55%H; 3.84%N; 21.17%Br.

EXAMPLE 9

A solution of 5.0 g of 10,11-dihydro-1'-methyl-11-oxospiro[dibenz(b,f)oxepin-10,4'-piperidine], free base of Example 8, in 40 ml of tetrahydrofuran is treated according to the procedure of Example 7 to provide a solid. The solid is recrystallized from an acetone-hexane mixture to provide colorless prisms, mp 180°–182° C. (dec), of 10,11-dihydro-11-hydroxy-1'-methylspiro[dibenz(b,f)oxepin-10,4'-piperidine].

Analysis: Calculated for $C_{19}H_{21}NO_2$: 77.25%C; 7.16%H; 4.74%N. Found: 77.22%C; 7.23%H; 4.67%N.

EXAMPLE 10

A mixture of 1.0 g of 10,11-dihydro-11-oxospiro[dibenz-(b,f)oxepin-10,4'-piperidine], free base of Example 3, 0.3 g of 2-propynyl chloride and 1 g of sodium bicarbonate in 15 ml of dimethylformamide is stirred at 70° C. for 16 hours. Thereafter, the mixture is successively diluted with ether, filtered, washed with water, dried and concentrated under vacuum leaving a pale yellowish oil. The oil is converted in ether to its hydrobromic acid salt which is recrystallized from a methyl alcohol-acetone-ether mixture to provide colorless granules, mp 241°–242° C., of 10,11-dihydro-11-oxo-1'-(2-propynyl)-spiro[dibenz(b,f)oxepin-10,4'-piperidine]hydrobromide.

Analysis: Calculated for $C_{21}H_{19}NO_2 \cdot HBr$: 63.32%C; 5.06%H; 3.52%N; 20.06%Br. Found: 63.54%C; 5.12%H; 3.46%N; 20.15%Br.

EXAMPLE 11

A mixture of 1.1 g of 10,11-dihydro-11-oxospiro[dibenz(b,f)oxepin-10,4'-piperidine], free base of Example 3, 0.63 g of β-bromoethyl alcohol and 1.1 g of sodium bicarbonate in 15 ml of dimethylformamide is stirred at 80° C. for 16 hours. Thereafter, the mixture is diluted with ether and water. The ether solution is extracted with an excess of 2 N hydrochloric acid. The acidic extract is basified with potassium carbonate, effecting a heavy oil. The oil is dissolved in ether and the ethereal solution is dried and concentrated to dryness, leaving a colorless oil which is converted, in ether, to its hydrobromic acid salt. The salt is recrystallized from a methyl alcohol-acetone-ether mixture to provide colorless prisms, mp 263°–266° C., of 10,11-dihydro-1'-(β-hydroxyethyl)-11-oxospiro[dibenz(b,f)oxepin-10,4'-piperidine]hydrobromide.

Analysis: Calculated for $C_{20}H_{21}NO_3$.HBr: 59.41%C; 5.48%H; 3.46%N; 19.76%Br. Found: 59.18%C; 5.63%H; 3.29%N; 19.70%Br.

EXAMPLE 12

A mixture of 2.0 g of 10,11-dihydro-11-oxospiro[dibenz(b,f)-oxepin-10,4'-piperidine], free base of Example 3, 0.74 g of chloromethylcyclopropane, 1.8 g of sodium bicarbonate and 1.8 g of potassium iodide in 15 ml of dimethylformamide is stirred at 70°–80° C. for 16 hours. The resulting suspension is permitted to cool before being diluted with ether and water. The organic phase is successively dried, filtered and concentrated under vacuum, leaving a viscous oil. The oil is dissolved in chloroform and the chloroform solution is passed through an alumina column, with ether as an eluant. The purified oil is dissolved in ether where it is converted to its hydrobromic acid salt which is recrystallized from a methyl alcohol-ether mixture to provide rhombic crystals, mp 258°–259° C., (dec) of 1'-cyclopropylmethyl-10,11-dihydro-11-oxospiro[dibenz(b,f)oxepin-10,4'-piperidine]hydrobromide.

Analysis: Calculated for $C_{22}H_{23}NO_2$.HBr: 63.77%C; 5.84%H; 3.38%N; 19.31%Br. Found: 63.52%C; 5.81%H; 3.34%N; 19.38%Br.

EXAMPLES 13 AND 14

Samples of 10,11-dihydro-11-oxospiro[dibenz(b,f)oxepin-10,4'-piperidine], free base of Example 3, are separately treated with phenoxypropyl bromide and 2-bromoethylbenzene according to the procedure of Example 12, to provide colorless prisms, mp 213°–215° C., (dec), of 10,11-dihydro-11-oxo-1'-(3-phenoxypropyl)-spiro[dibenz(b,f)oxepin-10,4'-piperidine]hydrobromide (from an ethyl alcohol-ether mixture), Example 13, and colorless prisms, mp>300° C., of 10,11-dihydro-11-oxo-1'-phenethylspiro[dibenz(b,f)-oxepin-10,4'-piperidine]hydrobromide (from an acetone-ether mixture), Example 14, respectively.

Analysis: Example 13: Calculated for $C_{27}H_{27}NO_3$.HBr: 65.59%C; 5.70%H; 2.83%N. Found: 65.37%C; 5.73%H; 2.80%N. Example 14: Calculated for $C_{26}H_{25}NO_2$.HBr: 67.20%C; 5.67%H; 3.30%N; 17.28%Br. Found: 66.69%C; 5.56%H; 3.17%N; 17.04%Br.

EXAMPLE 15

A mixture of 1.3 g of 10,11-dihydro-11-oxospiro[dibenz-(b,f)oxepin-10,4'-piperidine], free base of Example 3, 1.4 g of γ-chloro-4-fluorobutyrophenone ethylene glycol ketal, 1.0 g of sodium bicarbonate and 1.0 g of potassium iodide in 15 ml of dimethylformamide is stirred at 80° C. for 16 hours. Thereafter, the reaction mixture is filtered and the filtrate is concentrated leaving, as an oily residue, the compound 10,11-dihydro-1'-[4-fluorobutyrophenone]-11-oxospiro[dibenz(b,f)oxepin-10,4'-piperidine]-ethylene glycol ketal. The residue is dissolved in ethanolic hydrochloric acid, prepared by mixing 16 ml of absolute ethyl alcohol with 6 ml of 3 N hydrochloric acid, and the solution is stirred at ambient temperature for 16 hours. The acidic solution is basified with 40% sodium hydroxide, liberating an amine which is extracted into ether. The combined ether extracts are dried and then concentrated to dryness. The residue is passed through an alumina column, ether eluant, providing a colorless oil. The oil, in ether, is converted to its hydrobromic acid salt which is recrystallized from a methyl alcohol-ether mixture to provide colorless prisms, mp 260°–262° C., of 10,11-dihydro-1'-[3-(4-fluorobenzoyl)propyl]-11-oxospiro[dibenz(b,f)oxepin-10,4'-piperidine]hydrobromide.

Analysis: Calculated for $C_{23}H_{26}FNO_3$.HBr: 64.13%C; 5.29%H; 2.67%N; 15.24%Br. Found: 64.18%C; 5.28%H; 2.38%N; 15.49%Br.

EXAMPLE 16

A mixture of 2.5 g of 2-chloro-10,11-dihydro-11-oxospiro[dibenz(b,f)oxepin-10,4'-piperidine], free base of Example 5, 2.5 g of sodium bicarbonate, 2.0 g of potassium iodide and 0.8 g of chloromethylcyclopropane in 30 ml of dimethylformamide is stirred at 80° C. for 16 hours. Thereafter, the reaction mixture is cooled in an ice bath and then diluted with 90 ml of water. The aqueous phase is extracted twice with 40 ml portions of ether. The aqueous phase is adjusted to pH 9 with 58% ammonium hydroxide and extracted with an additional two 40 ml portions of ether. The combined ether extracts are successively washed twice with 40 ml portions of water, washed once with a 20 ml portion of a saturated sodium chloride solution and dried effecting an oil. The oil is passed through an alumina column, ether eluant, effecting a purified oil. This oil is dissolved in ether where it is converted to its hydrobromic acid salt, which is recrystallized from a methyl alcohol-acetone-ether mixture to provide a white powder, mp 305+° C., (dec) of 2-chloro-1'-cyclopropylmethyl-10,11-dihydro-11-oxo[dibenz(b,f)oxepin-10,4'-piperidine]hydrobromide.

Analysis: Calculated for $C_{22}H_{22}ClNO_2$.HBr: 58.88%C; 5.17%H; 3.12%N; 25.71% total h Found: 58.76%C; 5.35%H; 3.05%N; 25.73% total h

EXAMPLE 17

A mixture of 2.5 g of 2-chloro-10,11-dihydro-11-oxospiro[dibenz(b,f)oxepin-10,4'-piperidine], free base of Example 5, 2.5 g of sodium bicarbonate, 2.0 g of potassium iodide and 1.1 g of 2-propynyl bromide in 30 ml of dimethylformamide is treated according to the procedure of Example 16 to provide a chromatographed purified oil. The oil is placed under hexane and cooled to 0° C., effecting white crystals, which are recrystallized from benzene to provide a crystalline solid, mp 148°–150° C., of 2-chloro-10,11-dihydro-11-oxo-1'-(2-propynyl)-spiro[dibenz(b,f)oxepin-10,4'-piperidine].

Analysis: Calculated for $C_{21}H_{18}ClNO_2$: 71.69%C; 5.16%H; 3.98%N; 10.18%Cl. Found: 71.80%C; 5.27%H; 3.88%N; 10.18%Cl.

EXAMPLE 18

A mixture of 0.9 g of allyl bromide in dimethylformamide is added portionwise over 60 minutes to a mixture of 65° C. of 2.1 g of 2-chloro-10,11-dihydro-11-oxospiro[dibenz(b,f)oxepin-10,4'-piperidine], free base of Example 5 and 2.1 g of sodium bicarbonate in 15 ml of dimethylformamide. After total addition, the mixture is stirred at 60°–65° C. for 16 hours. Thereafter, the mixture is diluted with 75 ml of water and the biphasic mixture is extracted with 40 ml of ether. A white precipitate collected at the interface. The aqueous layer and interface material is extracted thrice with 40 ml portions of methylene chloride. The combined organic phases are successively washed twice with 50 ml portions of water, washed with a 25 ml portion of a saturated sodium chloride solution and dried effecting an oil. The oil is passed through an alumina column, ether eluant, to provide a purified oil which is dissolved in ether where it is converted to its hydrobromic acid salt. The salt is recrystallized from methyl alcohol to provide a white crystalline solid, mp 292°–295° C. (dec), of 1'-allyl-2-chloro-10,11-dihydro-11-oxospiro[dibenz(b,f)oxepin-10,4'-piperidine]hydrobromide.

Analysis: Calculated for $C_{21}H_{20}ClNO_2 \cdot HBr$: 58.01%C; 4.87%H; 3.22%N; 26.53% total halogen Found: 58.02%C; 4.93%H; 3.16%N; 26.45% total halogen

EXAMPLE 19

A mixture of 1.2 g of ethyl iodide in 10 ml of dimethylformamide is added portionwise over a 30 minute span to a mixture at 80° C. of 2.1 g of 2-chloro-10,11-dihydro-11-oxospiro[dibenz(b,f)oxepin-10,4'-piperidine], free base of Example 5. After total addition, the reaction mixture is cooled to 0° C. before being diluted with 75 ml of water and then extracted with a 40 ml portion of ether. Both phases are filtered through paper and the filter cake is dissolved in 75 ml of chloroform. The chloroform solution is washed with water and then dried, leaving an oil. The aqueous phase is extracted four times with 40 ml portions of ether. The combined ether extracts are successively washed with two 40 ml portions of water, then washed with one 20 ml portion of a saturated sodium chloride solution, effecting an oil. This oil and the previous oil are passed through an alumina column, ether eluant, providing a purified oil. This oil is dissolved in ether where it is converted to its hydrobromic acid salt, a white powder, which is recrystallized from methyl alcohol to provide clear rhombic plates, mp 303°–304° C., of 2-chloro-1'-ethyl-10,11-dihydro-11-oxospiro[dibenz(b,f)oxepin-10,4'-piperidine]hydrobromide.

Analysis: Calculated for $C_{20}H_{20}ClNO_2 \cdot HBr$: 56.82%C; 5.01%H; 3.31%N; 27.29% total halogen Found: 56.94%C; 5.16%H; 3.28%N; 27.07% total halogen

EXAMPLE 20

A mixture of 2.1 g of 2-chloro-10,11-dihydro-11-oxospiro[dibenz(b,f)oxepin-10,4'-piperidine], free base of Example 5, and 2.1 g of sodium bicarbonate in 15 ml of dimethylformamide is stirred at 85° C. before adding portionwise over a 30 minute span a mixture of 1.3 g of iodopropane in 10 ml of dimethylformamide. After total addition, the reaction is stirred at 80°–85° C. for 16 hours and then permitted to stand for 48 hours at ambient temperature. Thereafter, the reaction mixture is diluted with 75 ml of water and the diluted mixture is extracted thrice with 40 ml portions of ether. The combined ether extracts are successively washed twice with 30 ml portions of water, washed with a 20 ml portion of a saturated sodium chloride solution and dried, effecting an oil. The oil is dissolved in an ethyl alcohol-3 N hydrochloric acid (2:1) mixture. The acidic solution is basified to pH 9 with a 58% ammonium hydroxide solution before being extracted four times with 40 ml portions of ether, effecting an oil. The oil is passed through an alumina column, ether eluant, to provide a purified oil. This oil is dissolved in ether where it is converted to its hydrobromic acid salt. Methyl alcohol is added to the ethereal solution, the ether is removed with heating and then acetone is added to provide a white powder, mp 315°–316° C., of 2-chloro-10,11-dihydro-11-oxo-1'-propylspiro[dibenz(b,f)oxepin-10,4'-piperidine]hydrobromide.

Analysis: Calculated for $C_{21}H_{22}ClNO_2 \cdot HBr$: 57.75%C; 5.31%H; 3.21%N; 26.42% total halogen Found: 58.02%C; 5.38%H; 3.29%N; 26.36% total halogen

EXAMPLE 21

A mixture of 1.0 g of 1-bromo-3-methyl-2-butene in 10 ml of dimethylformamide is added portionwise over a 20 minute span to a stirred mixture at 80° C. of 1.9 g of 2-chloro-10,11-dihydro-11-oxospiro[dibenz(b,f)oxepin-10,4'-piperidine], free base of Example 5, and 1.9 g of sodium bicarbonate in 15 ml of dimethylformamide. After total addition, the mixture is stirred at 80° C. for 16 hours. Thereafter, the mixture is diluted with 75 ml of water and the diluted mixture is extracted thrice with 40 ml portions of ether. The combined ether extracts are successively washed with two 30 ml portions of water, then with 20 ml of a saturated sodium chloride solution and dried, effecting an oil. The oil is chromatographed on four 20×20 cm preparative layer plates of silica gel F 254 in a 10% methyl alcoholbenzene mixture. A band (Rf 0.25–0.61) is eluted to provide an oil. The oil is dissolved in ether, where it is converted to its hydrobromic acid salt. The salt is recrystallized from a methyl alcohol-acetone-ether mixture to provide a white powder, mp 266.5°–267.5° C. (dec), of 2-chloro-10,11-dihydro-1'-(2-methyl-2-butenyl)-11-oxospiro[dibenz(b,f)oxepin-10,4'-piperidine]hydrobromide.

Analysis: Calculated for $C_{23}H_{24}ClNO_2 \cdot HBr$: 59.69%C; 5.45%H; 3.03%N; 24.93% total halogen Found: 59.62%C; 5.36%H; 2.99%N; 24.66% total halogen

EXAMPLE 22

A solution of 0.93 g of 2-bromoethyl alcohol in 10 ml of dimethylformamide is added portionwise over a 30 minute span to a stirring mixture, at 80° C., of 2.1 g of 2-chloro-10,11-dihydro-11-oxospiro[dibenz(b,e)oxepin-10,4'-piperidine], free base of Example 5, 2.1 g of sodium bicarbonate and 1.7 g of potassium iodide in 15 ml of dimethylformamide. After total addition, the reaction mixture is stirred at 80°–85° C. for 16 hours. Thereafter, the mixture is diluted with 75 ml of water and the diluted mixture is extracted thrice with 40 ml portions of ether. The combined ether extracts are successively washed twice with 30 ml portions of water and extracted twice with 36 ml portions of 2 N hydrochloric acid. The combined acidic mixture is cooled and then basified to pH 9 with 58% ammonium hydroxide. The basic mixture is extracted thrice with 40 ml portions of ether and the combined ether extracts are successively washed with one 40 ml portion of water and dried effecting an oil. The oil is passed through an alumina column, a methyl alcohol-ether (1:1) mixture eluant, providing a solid. The solid is dissolved in ether and filtered, providing a glassy solid which is dissolved in a 15% acetone-ether mixture where it is converted to its hydrobromic acid salt, which is recrystallized from a methyl alcohol-acetone-ether mixture to provide a white powder, mp 240°–242° C. of 2-chloro-10,11-dihydro-1'-(2-hydroxyethyl)-11-oxospiro-[dibenz(b,f)oxepin-10,4'-piperidine]hydrobromide.

Analysis: Calculated for $C_{20}H_{20}ClNO_3 \cdot HBr$: 54.75%C; 4.82%H; 3.19%N; 26.29% total halogen Found: 54.89%C; 5.07%H; 3.10%N; 26.18% total halogen

EXAMPLE 23

A mixture of 2.1 g of 2-chloro-10,11-dihydro-11-oxospiro[dibenz(b,f)oxepin-10,4′-piperidine], free base of Example 5, 2.1 g of sodium bicarbonate and 1.7 g of potassium iodide and 1.4 g of (2-bromoethyl)benzene in 25 ml of dimethylformamide is stirred at 50°–65° C. for 18 hours. Thereafter, the mixture is diluted with 40 ml portions of ether. The combined ether extracts are successively washed twice with 30 ml portions of water, washed once with 20 ml of a saturated sodium chloride solution and dried, leaving an oil. The oil is passed through an alumina column, ether eluant, providing a purified oil. This oil is treated with hexane and the hexane mixture is cooled and filtered, providing a white crystalline material which is recrystallized from acetone to provide a white solid, mp 136.5°–138° C., of 2-chloro-10,11-dihydro-11-oxo-1′-(β-phenylethyl)spiro[dibenz(b,f)oxepin-10,4′-piperidine].

Analysis: Calculated for $C_{26}H_{24}ClNO_2$: 74.72%C; 5.79%H; 3.35%N; 8.48%Cl. Found: 74.97%C; 5.92%H; 3.44%N; 8.38%Cl.

EXAMPLE 24

A solution of 1.6 g of 3-phenoxypropyl bromide in 10 ml of dimethylformamide is added, portionwise over a 20 minute span, to a mixture, at 80° C., of 2.1 g of 2-chloro-10,11-dihydro-11-oxospiro[dibenz(b,f)oxepin-10,4′-piperidine], free base of Example 5, 2.1 g of sodium bicarbonate and 1.7 g of potassium iodide in 15 ml of dimethylformamide. After total addition, the reaction mixture is stirred at 80°–85° C. for 16 hours. Thereafter, the mixture is cooled in an ice bath before being diluted with 75 ml of water. The diluted mixture is extracted with 40 ml of ether and both phases (organic and aqueous) are passed through filter paper. The filtered aqueous phase is extracted thrice with 40 ml portions of ether and the combined ether extracts are successively washed twice with 40 ml portions of ether and the combined ether extracts are successively washed twice with 40 ml portions of water, washed once with 20 ml of a saturated sodium chloride solution and dried leaving an oil. The crude oil is purified by passing it through an alumina column, ether eluant. The purified oil is dissolved in ether and the ethereal solution is permitted to stand, effecting a white precipitate. The precipitate is collected by filtration and then washed with ether, providing a white crystalline material, mp 105°–107° C., of 2-chloro-10,11-dihydro-11-oxo-1′-(3-phenoxypropyl)spiro[dibenz(b,f)oxepin-10,4′-piperidine].

Analysis: Calculated for $C_{27}H_{26}ClNO_3$: 72.39%C; 5.85%H; 3.13%N; 7.91%Cl. Found: 72.33%C; 5.94%H; 3.13%N; 8.02%Cl.

EXAMPLE 25

A mixture of 1.8 g of 4-chloro-p-fluorobutyrophenone ethylene ketal in 10 ml of dimethylformamide is added portionwise over a 30 minute span to a mixture, at 85° C., of 2.1 g of 2-chloro-10,11-dihydro-11-oxospiro[dibenz(b,f)oxepin-10,4′-piperidine], free base of Example 5, 1.7 g of potassium iodide and 2.1 g of sodium bicarbonate in 15 ml of dimethylformamide. After total addition, the reaction mixture is stirred at 80°–85° C. for 16 hours and then permitted to stand for 48 hours. Thereafter, the reaction mixture is diluted with 75 ml of water and the diluted mixture is extracted thrice with 40 ml portions of ether. The combined ether extracts are washed twice with 30 ml portions of water and then rotary evaporated, providing as a glassy residue, the compound 2-chloro-1′-[4-fluorobutyrophenone]-10,11-dihydro-11-oxospiro[dibenz(b,f)oxepin-10,4′-piperidine]ethylene glycol ketal. The residue is dissolved in a mixture of 55 ml of ethyl alcohol and 21 ml of 3 N hydrochloric acid. The acidic solution is stirred at ambient temperature for 19 hours. The well stirred mixture is cooled in an ice bath and then basified to pH 9 with 58% ammonium hydroxide. The basic mixture is extracted thrice with 40 ml portions of ether and the combined ether extracts are successively washed twice with 30 ml portions of water, washed once with 20 ml of a saturated sodium chloride solution, dried and evaporated to dryness, providing an oil. The oil is purified by passing through an alumina column, ether eluant. The purified oil is dissolved in ether where it is precipitated as its hydrobromic acid salt. The salt is washed with ether and then recrystallized from an acetone-ether mixture to provide a white powder, mp 220°–221° C., of 2-chloro-1′-[3-(4-fluorobenzoyl)-propyl]-10,11-dihydro-11-oxospiro[dibenz(b,f)oxepin-10,4′-piperidine]hydrobromide.

Analysis: Calculated for $C_{28}H_{25}ClFNO_3 \cdot HBr$: 60.17%C; 4.69%H; 2.51%N; 20.64% total hal. Found: 60.10%C; 4.66%H; 2.52%N; 20.68% total hal.

EXAMPLE 26 a.

A mixture of 147 g of iodobenzoic acid, 45.5 g of potassium carbonate in 57 ml of nitrobenzene is maintained with stirring at 160° C. for 40 minutes. Thereafter, 46.5 g of additional potassium carbonate is added which is followed by the addition of 73.1 g of 4-fluorophenol, another 46.5 g of potassium carbonate and 0.35 g of copper powder. The reaction mixture is stirred in a 160° C. bath for 45 minutes. The resulting solid is collected and then cooled to 0° C. before being mixed with 100 ml of water and 200 ml of 6 N hydrochloric acid. The aqueous mixture is then diluted to 1 liter total volume before being stirred with 450 ml of chloroform. The resulting white solid is collected and washed successively with chloroform and water. The solid is dissolved in hot acetone and the acetone solution is successively filtered and cooled to provide a white crystalline product. The product is recrystallized from acetone and then converted to a salt with potassium carbonate. The salt is dissolved in water and the aqueous solution is acidified with 1 N hydrochloric acid to provide white crystals, mp 143°–146° C., of 2-(4-fluorophenoxy)benzoic acid.

b.

36.1 mls of 70% sodium-(2-methoxyethyl)aluminum hydride in benzene are added dropwise over a one hour span to a stirring mixture of 15 g of 2-(4-fluorophenoxy)benzoic acid in 150 ml of benzene under nitrogen at ambient temperature. After total addition, the reaction mixture is stirred for an additional 30 minutes and then permitted to stand for 4 days. Thereafter, the reaction mixture is cooled to 0° C. before 100 mls of 10% sodium hydroxide are added with stirring. Following this addition, the layers separate and the aqueous layer is extracted twice with 100 ml portions of benzene. The combined benzene solutions are successively washed twice with 100 ml portions of water, washed once with 60 ml of a saturated sodium chloride solution and dried, providing a clear yellow oil. The oil is distilled at 118.5°–121.5° C. and 0.07 mm pressure to provide the clear, colorles liquid, 2-(4-fluorophenoxy)benzyl alcohol.

c.

8.5 g of thionyl chloride are added dropwise over a 10 minutes span to a stirring mixture of 13.0 g of 2-(4-fluorophenoxy)benzyl alcohol in 80 ml of benzene at ambient temperature. After total addition, the reaction mixture is stirred for 16 hours before being carefully poured onto 350 ml of crushed ice containing 8 ml of sodium bicarbonate. The mixture is stirred until the ice melts. The layers separate and the benzene layer is successively washed twice with 40 ml portions of a half saturated sodium bicarbonate solution, washed twice with 40 ml portions of water, washed once with a 25 ml portion of a saturated sodium chloride solution, dried and rotary evaporated to provide a clear liquid. The liquid is distilled at 106°–109° C. and 0.16 mm to provide a clear colorless liquid of 2-(4-fluorophenoxy)benzyl chloride.

d.

12.0 g of 2-(4-fluorophenoxy)benzyl chloride are added portionwise over a 30 minute span to a mixture of 2.9 g of sodium cyanide in 120 ml of dimethylsulfoxide. After total addition, the reaction mixture is stirred for 26 hours before being poured onto 150–200 ml of crushed ice. The mixture is extracted four times with 70 ml portions of ether and the combined ether extracts are successively washed four times with 50 ml portions of water, washed once with 25 ml of saturated sodium chloride solution and dried, providing a clear oil. The oil is distilled at 128.5°–130° C. and 0.1 mm to provide 2-(4-fluorophenoxy)benzyl cyanide.

e.

2.3 g of 99% sodium hydride are slowly added to a mixture, under nitrogen, of 4.3 g of 2-(4-fluorophenoxy)-benzyl cyanide in 30 mls of dimethylsulfoxide. After total addition, the mixture is stirred for an additional five minutes and then a mixture of 3.9 g of 95% mechlorethamine hydrochloride in 20 ml of dimethylsulfoxide is added portionwise over a 40 minute span. After this addition, the reaction is stirred for 1 hour in a hot water bath at 70° C. and then permitted to stand at ambient temperature for 16 hours. The cooled reaction mixture is poured onto 150 ml of crushed ice and the diluted mixture is extracted thrice with 60 ml portions of ether. The combined ether extracts are washed with 25 ml of saturated sodium chloride solution and dried, providing a yellow solid. The solid is recrystallized from cyclohexane leaving a white solid, mp 106°–107.5° C. of 4-cyano-4-[2-(4-fluorophenoxy)phenyl]-1-methylpiperidine.

Analysis: Calculated for $C_{19}H_{19}FN_2O$: 73.52%C; 6.16%H; 9.03%N; 6.12%F. Found: 73.47%C; 6.04%H; 8.99%N; 6.23%F.

f.

A mixture of 4.4 g of 4-cyano-4-[2-(4-fluorophenoxy)-phenyl]-1-methylpiperidine in 95 ml of 48% hydrobromic acid is stirred at reflux for 16 hours. Thereafter, the mixture is diluted with 300 ml of water before being rotary evaporated at 80° C. to provide a tan solid. The solid is swirled with 300 ml of water and dissolved by raising the pH to 9 with concentrated ammonium hydroxide. The solution is permitted to stand for 96 hours. The is was slowly lowered to 4 and then returned to 9 with concentrated ammonium hydroxide. The volume is reduced by rotary evaporation at 80° C. until a precipitate appears. Thereafter, the reaction mixture is cooled and the precipitate collected by filtration and then washed with water. The precipitate is sequentially washed with acetone, treated with 1 ml of 48% hydrobromic acid diluted with 20 ml of water and applied to a Bio Rad A 650 W-X8 cation exchange resin, eluted with 5.8–8.7% ammonium hydroxide to provide a white powder, mp 284°–286° C., of 4-[2-(4-fluorophenoxyphenyl)]-1-methylpiperidine-4-carboxylic acid.

Analysis: Calculated for $C_{19}H_{20}FNO_3$: 69.28%C; 6.12%H; 4.25%N; 5.77%F. Found: 69.04%C; 5.98%H; 4.34%N; 5.63%F.

g.

A mixture of 2.5 g of 4-[2-(4-fluorophenoxy)phenyl]-1-methylpiperidine-4-carboxylic acid and 24 ml of polyphosphoric acid is stirred under nitrogen for 2 hours in a 100°–115° C. bath. Thereafter, the mixture is cooled in an ice bath before diluting with 50 ml of water and 15 ml of ice. The cooled diluted mixture is basified to pH 9–10 with 58% ammonium hydroxide and the basified mixture is extracted thrice with 50 ml portions of an ether-methylene chloride (2:1) mixture. The extracts are combined and washed sequentially, once with 75 ml of a 10% sodium hydroxide solution, then with 75 ml of water and finally with 20 ml of saturated sodium chloride solution, and then dried. The dried solution is concentrated to dryness, leaving an oil which is chromatographed through a silica gel column, methyl alcohol-methylene chloride (1:9) mixture eluant, to provide a purified oil. The oil, in ether, is converted to its hydrobromic acid salt. The salt is recrystallized repeatedly from a methyl alcoholether mixture to provide white crystals, mp 294.0°–295.5° C., of 2-fluoro-10,11-dihydro-1'-methyl-11-oxospiro[dibenz(b,f)oxepin-10,4'-piperidine]hydrobromide.

Analysis: Calculated for $C_{19}H_{18}FNO_2.HBr$: 58.17%C; 4.88%H; 3.57%N; 4.84%F. Found: 58.08%C; 4.79%H; 3.59%N; 4.71%F.

EXAMPLE 27

A mixture of 3.0 g of 2-fluoro-10,11-dihydro-1'-methyl-11-oxospiro[dibenz(b,f)oxepin-10,4'-piperidine], free base of Example 26, in 10 ml of methylene chloride is added portionwise over a 15 minute span to a mixture of 1.3 g of cyanogen bromide and 6.4 g of potassium carbonate in 17 ml of methylene chloride. After total addition, the mixture is stirred at reflux for 2 hours and then permitted to cool to ambient temperature. Thereafter, the mixture is filtered and then evaporated to dryness and the residue is taken up in methyl alcohol. The alcoholic solution is refluxed and acetone and ether are then added, effecting a precipitate. The mixture is filtered and the supernatant liquid is evaporated, leaving a glassy solid which is chromatographed through a silica gel column, ether-methylene chloride (1:1) mixture, eluant, to provide a purer product. The product is initially dissolved in acetone and then diluted with ether and pentane followed by repeated recrystallizations from an acetone-ether-pentane mixture to provide a white crystalline powder, mp 105°–106° C., of 1′-cyano-2-fluoro-10,11-dihydro-11-oxospiro[dibenz(b,f)oxepin-10,4′-piperidine].

Analysis: Calculated for $C_{19}H_{15}FN_2O_2$: 70.79%C; 4.69%H; 8.69%N; 5.89%F. Found: 70.59%C; 4.81%H; 8.63%N; 5.97%F.

EXAMPLE 28

A mixture of 1.8 g of 1′-cyano-2-fluoro-10,11-dihydro-11-oxospiro[dibenz(b,f)oxepin-10,4′-piperidine], Example 27, in 11 ml of acetic acid and 21 ml of 3 N hydrochloric acid is stirred in a 125°–130° C. bath for 20 hours. Thereafter, the mixture is diluted with 25 ml and rotary evaporated to dryness. The residue is taken up in 25 ml of water and the water removed by rotary evaporation, leaving a white solid. The solid is taken up in 25 ml of water and the aqueous mixture is cooled to 0° C. The precipitate is collected by filtration and then washed sequentially with water and ether before being dried. The product is recrystallized repeatedly from a methyl alcohol-acetone-ether mixture to provide a white granular solid, mp 297°–299° C., of 2-fluoro-10,11-dihydro-11-oxospiro[dibenz(b,f)oxepin-10,4′-piperidine]hydrochloride.

Analysis: Calculated for $C_{18}H_{16}FNO_2 \cdot HCl$: 64.77%C; 5.13%H; 4.20%N; 5.69%F. Found: 64.50%C; 5.11%H; 4.10%N; 5.71%F.

EXAMPLE 29 a.

A mixture of 19.8 g of 4-cyano-4-[2-(4-fluorophenoxy)-phenyl]-1-methylpiperidine, Example 26(c), in 200 ml of chloroform is added portionwise over a 15 minute span to a mixture of 33.4 g of 97% cyanogen bromide and 130 g of potassium carbonate in 250 ml of chloroform. After total addition, the mixture is successively refluxed for 16 hours, cooled, filtered, washed thrice with 300 ml portions of water and once with 50 ml of saturated sodium chloride solution and dried, providing a clear, pale yellow oil which crystallizes on standing. The solid is dissolved in benzene and the benzene solution is boiled after powdered charcoal is added. The mixture is filtered through celite, and then its volume is reduced and rediluted with hexane, effecting a white crystalline powder, mp 107.5°–109.5° C., of 1,4-dicyano-4-[2-(4-fluorophenoxy)phenyl]piperidine.

b.

A mixture of 12.0 g of 1,4-dicyano-4-[2-(4-fluorophenoxy)phenyl]piperidine, Example 28, in 240 ml of 48% hydrobromic acid is stirred in a 150° C. bath for 40 hours before adding 120 ml of glacial acetic acid and continuing the stirring at the same temperature for 30 additional hours. Thereafter, the solution is permitted to stand for 64 hours before the excess is distilled off, leaving a paste-like residue. The residue is taken up in 50 ml of water and the aqueous mixture is rotary evaporated, leaving a solid which, when washed with water and then ether, becomes a tan-grey powder. The powder is dissolved in 250 ml of methyl alcohol and the alcoholic solution is boiled after charcoal is added, giving a white crystalline powder. The powder is recrystallized three times from a methyl alcohol-ether mixture to provide a white crystalline powder. The powder is recrystallized once from an ethyl alcohol-water mixture and dried to provide the product, melting range 180°–250° C. (dec), of 4-[2-(4-fluorophenoxy)phenyl]piperidine-4-carboxylic acid hydrobromide.

c.

A mixture of 0.7 g of 4-[2-(4-fluorophenoxy)phenyl]-piperidine-4-carboxylic acid and 0.83 ml of acetic anhydride in 4.2 ml of pyridine is stirred at reflux for 4 hours. Thereafter, the excess pyridine is removed by rotary evaporation and the residue is taken up in 10 ml of water where it is treated with 10 ml of 1 N hydrochloric acid. The acidic mixture is extracted thrice with 20 ml portions of an ether-benzene (1:1) mixture and the combined extracts are successively washed twice with 40 ml portions of water, washed once with 7 ml of saturated copper sulfate solution, washed once with 15 ml of saturated sodium chloride solution and dried to provide a glassy solid. The solid is recrystallized from an acetone-ether (1:4) mixture and then repeatedly from acetone to provide a white crystalline powder, mp 192.5°–193.5° C., of 1-acetyl-4-[2-(4-fluorophenoxy)-phenyl]piperidine-4-carboxylic acid.

d.

0.13 ml of freshly distilled thionyl chloride are added to a mixture of 0.3 g of 1-acetyl-4-[2-(4-fluorophenoxy)-phenyl]piperidine-4-carboxylic acid in 3 ml of methylene chloride. The resulting pink solution is stirred for 155 minutes before being diluted with 7.5 ml of methylene chloride. The reaction solution is added dropwise to 0.17 g of aluminum chloride. Thereafter, the reaction is stirred for 15 minutes and then refluxed for three hours. The refluxed mixture is stirred for 72 hours before a sequential addition of ice, 25 ml of water and 25 ml of chloroform. The mixture is shaken and then the layers separate. The aqueous layer is extracted twice with 25 ml portions of chloroform and the combined chloroform solutions are successively washed with one 20 ml portion of a 10% sodium hydroxide solution, two 30 ml portions of water and 1 ml portion of a saturated sodium chloride solution, dried and evaporated, leaving an oil. The oil is chromatographed on 20×20 cm. preparative, thick layer, silica gel plates with an acetone-ether-methylene chloride (1:1:1) mixture. The high Rf band is discarded and the major band is concentrated to a glassy solid. The solid is dissolved in benzene and diluted with hexane and then the solvent is removed, leaving a white crystalline powder. The powder is recrystallized from a benzene-hexane mixture to provide the product, mp 143°–145° C., of 1′-acetyl-2-fluoro-10,11-dihydro-11-oxospiro[dibenz(b,f)oxepin-10,4′-piperidine].

Analysis: Calculated for $C_{20}H_{18}FNO_3$: 70.78%C; 5.36%H; 4.13%N. Found: 70.70%C; 5.15%H; 3.94%N.

Other compounds of the invention can be prepared according to procedures consistent with the foregoing examples.

We claim:

1. A compound of the formula

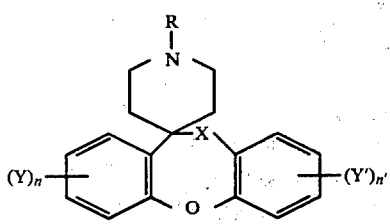

or a pharmaceutically acceptable acid addition salt thereof, in which R is hydrogen, alkyl of 1 to 6 carbon atoms, alkenyl of 2 to 6 carbon atoms, alkynyl of 2 to 6 carbon atoms, hydroxyalkyl, cycloalkylalkyl in which the cycloalkyl moiety contains 3 to 7 carbon atoms, phenalkyl unsubstituted or substituted by one or more substituents selected from the group consisting of nitro, amino, chlorine, fluorine, bromine, methoxy, loweralkyl and trifluoromethyl, phenoxyalkyl unsubstituted or substituted by one or more substituents selected from the group consisting of nitro, amino, chlorine, fluorine, bromine, methoxy, loweralkyl and trifluoromethyl, alkanoyl of 2 to 6 carbon atoms, benzoylalkyl unsubstituted or substituted by one or more substituents selected from the group consisting of nitro, amino, chlorine, fluorine, bromine, methoxy, loweralkyl and trifluoromethyl, cyano, ethylene glycol ketal of the formula

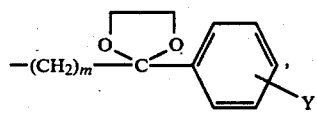

the alkyl moiety of the hydroxyalkyl, cycloalkylalkyl, phenalkyl, phenoxyalkyl and benzoylalkyl containing 1 to 6 carbon atoms;

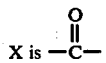

when R is as defined previously, or

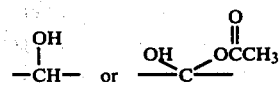

when R is alkanoyl of 2 to 6 carbon atoms, methyl or cyano; Y and Y' are the same or different and each can be hydrogen, chlorine, fluorine, bromine, methoxy, methylthio or trifluoromethyl; n and n' are the same or different and each can be an integer from 1 to 2, inclusive; and m is an integer from 1 to 4; inclusive.

2. A compound as defined in claim 1 in which Y is hydrogen.

3. A compound as defined in claim 1 in which Y' is hydrogen, chlorine or fluorine and n' is 1.

4. A compound as defined in claim 1 in which Y is hydrogen and Y' is hydrogen, chlorine or fluorine and n' is 1.

5. A compound defined in claim 1 in which X is

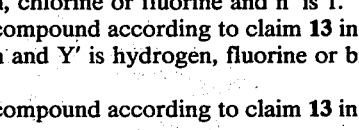

6. A compound according to claim 5 in which Y is hydrogen.

7. A compound according to claim 5 in which Y' is hydrogen, chlorine or fluorine and n' is 1.

8. A compound according to claim 5 in which Y is hydrogen and Y' is hydrogen, chlorine or fluorine.

9. A compound defined in claim 5 in which R is hydrogen, alkyl of 1 to 6 carbon atoms, alkenyl of 2 to 6 carbon atoms, alkynyl of 2 to 6 carbon atoms, cycloalkylalkyl, the cycloalkyl moiety containing 3 to 7 carbon atoms, phenalkyl unsubstituted or substituted by one or more substituents selected from the group consisting of nitro, amino, chlorine, fluorine, bromine, methoxy, loweralkyl and trifluoromethyl or benzoylloweralkyl unsubstituted or substituted by one or more substituents selected from the group consisting of nitro, amino, chlorine, fluorine, bromine, methoxy, loweralkyl and trifluoromethyl, the alkyl moiety of the cycloalkylalkyl and phenalkyl containing 1 to 6 carbon atoms.

10. A compound according to claim 9 in which Y is hydrogen.

11. A compound according to claim 10 in which Y' is hydrogen, chlorine or fluorine and n' is 1.

12. A compound according to claim 10 in which Y is hydrogen and Y' is hydrogen, chlorine or fluorine and n' is 1.

13. A compound as defined in claim 1 in which R is hydrogen, alkyl of from 1 to 3 carbon atoms, alkenyl of 2 or 3 carbon atoms, alkynyl of 2 or 3 carbon atoms, hydroxyethyl, cycloalkylalkyl of from 4 to 8 carbon atoms, phenoxyalkyl unsubstituted or substituted by one or more substituents selected from the group consisting of nitro, amino, chlorine, fluorine, bromine, methoxy, loweralkyl and trifluoromethyl in which the alkyl moiety of the phenoxyalkyl contains from 1 to 6 carbon atoms, phenylalkyl in which the alkyl moiety contains from 1 to 3 carbon atoms, benzoylalkyl unsubstituted or substituted by one or more substituents selected from the group consisting of nitro, amino, chlorine, fluorine, bromine, methoxy, loweralkyl and trifluoromethyl in which the alkyl moiety of the benzoylalkyl contains from 1 to 3 carbon atoms, cyano or ethylene glycol ketal of the formula

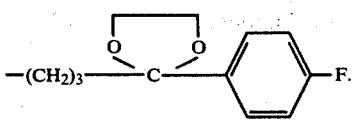

14. A compound according to claim 13 in which Y is hydrogen.

15. A compound according to claim 13 in which Y' is hydrogen, chlorine or fluorine and n' is 1.

16. A compound according to claim 13 in which Y is hydrogen and Y' is hydrogen, fluorine or bromine and n' is 1.

17. A compound according to claim 13 in which X is

18. A compound according to claim 17 in which Y is hydrogen.

19. A compound according to claim 17 in which Y' is hydrogen, chlorine or fluorine and n' is 1.

20. A compound according to claim 17 in which Y is hydrogen and Y' is hydrogen, chlorine or fluorine and n' is 1.

21. The compound of claim 1 which is 2-chloro-10,11-dihydro-1'-methyl-11-oxospiro[dibenz(b,f)oxepin-10,4'-piperidine] or a pharmaceutically acceptable acid addition salt thereof.

22. The compound of claim 1 which is 2-chloro-10,11-dihydro-11-oxospiro[dibenz(b,f)oxepin-10,4'-piperidine] or a pharmaceutically acceptable acid addition salt thereof.

23. The compound of claim 1 which is 2-chloro-1'-ethyl-10,11-dihydro-11-oxospiro[dibenz(b,f)oxepin-10,4'-piperidine] or a pharmaceutically acceptable acid addition salt thereof.

24. The compound of claim 1 which is 1'-[3-(4-fluorobenzoyl)propyl]-10,11-dihydro-11-oxospiro[dibenz(b,f)oxepin-10,4'-piperidine] or a pharmaceutically acceptable acid addition salt thereof.

25. The compound of claim 1 which is 10,11-dihydro-11'-oxo-1'-(2-propynyl)spiro[dibenz(b,f)oxepin-10,4'-piperidine] or a pharmaceutically acceptable acid addition salt thereof.

26. The compound of claim 1 which is 2-chloro-1'-cyclopropylmethyl-10,11-dihydro-11-oxospiro[dibenz(b,f)oxepin-10,4'-piperidine] or a pharmaceutically acceptable acid addition salt thereof.

27. The compound of claim 1 which is 2-fluoro-10,11-dihydro-11-oxospiro[dibenz(b,f)oxepin-10,4'-piperidine] or a pharmaceutically acceptable acid addition salt thereof.

28. The compound of claim 1 which is 2-fluoro-10,11-dihydro-1'-methyl-11-oxospiro[dibenz(b,f)oxepin-10,4'-piperidine] or a pharmaceutically acceptable acid addition salt thereof.

29. A method of alleviating pain in a patient which comprises administering to a patient a pharmaceutically effective amount of a compound of claim 1.

30. A method of depressing the central nervous system of a patient which comprises administering to a patient a pharmaceutically effective amount of a compound of claim 1.

31. A method of treating convulsions of a patient which comprises administering to a patient a pharmaceutically effective amount of a compound of claim 1.

32. A pharmaceutical composition comprising between 0.5 and 70% by weight of a compound defined in claim 1 and a pharmaceutically acceptable carrier therefor.

33. A method for preparing a compound of the formula

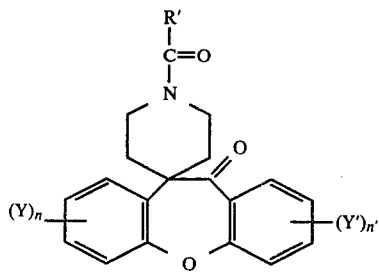

in which R' is loweralkyl, Y and Y' are the same or different and each can be hydrogen, chlorine, fluorine, bromine, methoxy, methylthio or trifluoromethyl; and n and n' are the same or different and each can be an integer from 1 to 2, inclusive, which comprises subjecting a 2-phenoxyphenyl acetonitrile of the formula

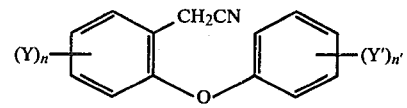

to bisalkylation with mechlorethamine hydrochloride in the presence of a strong base, at a reaction temperature of from about ambient to 85° C. to provide a 4-cyano-1-methyl-4-(2-phenoxyphenyl)piperidine of the formula

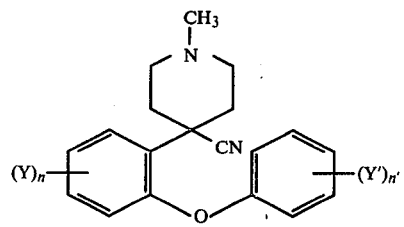

treating said 4-cyano-1-methyl-4-(2-phenoxyphenyl)piperidine in accordance with the first step of the von Braun reaction to form a 1,4-dicyano-4-(2-phenoxyphenyl)piperidine of the formula

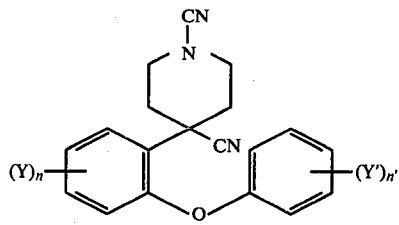

subjecting said 1,4-dicyano-4-(2-phenoxyphenyl)piperidine to acid hydrolysis to yield a 4-(2-phenoxyphenyl)piperidine-4-carboxylic acid of the formula

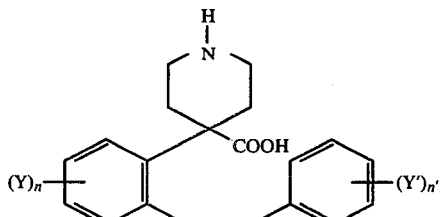

acylating said 4-(2-phenoxyphenyl)piperidine-4-carboxylic acid with an alkanoyl halide or anhydride in the presence of a basic solvent or an acid scavenger to provide a 1-alkanoyl-4-(2-phenoxyphenyl)piperidine-4-carboxylic acid of the formula

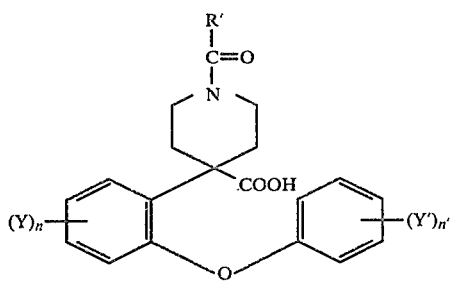

reacting said 1-alkanoyl-4-(2-phenoxyphenyl)piperidine-4-carboxylic acid with a thionyl halide by heating on a steam bath for about 5 minutes to yield a 1-alkanoyl-4-carbonylhalide of the formula

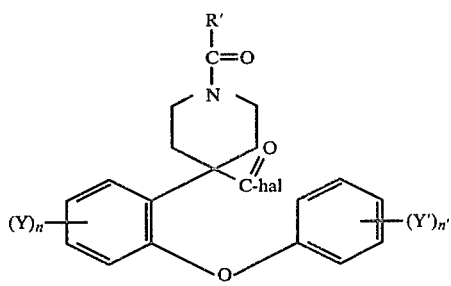

and cycliacylating said 1-alkanoyl-4-(2-phenoxyphenyl)piperidine-4-carbonylhalide.

34. The method of claim 33 in which said cycliacylating is carried out under modified Friedel-Crafts conditions with a Lewis acid catalyst such as aluminum chloride or ferric chloride.

35. The method of claim 34 in which methylene chloride is the solvent and the reaction temperature is from about 15° C. to about 150° C.

36. A method for preparing a compound of the formula

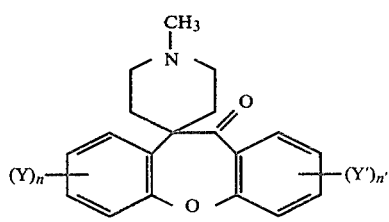

in which Y and Y' are the same or different and each can be hydrogen, chlorine, fluorine, bromine, methoxy, methylthio or trifluoromethyl and n and n' are the same or different and each can be an integer from 1 or 2, inclusive, which comprises subjecting a 4-cyano-1-methyl-4-(2-phenoxyphenyl)piperidine of the formula

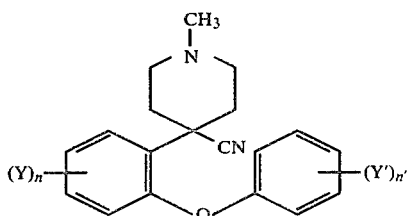

to acid hydrolysis to provide a corresponding carboxylic acid of the formula

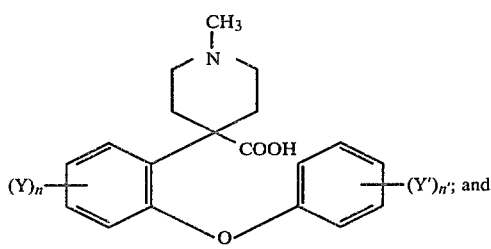

cycliacylating said carboxylic acid.

37. The method of claim 36 in which said cycliacylating is carried out under modified Friedel-Crafts conditions with a Lewis acid catalyst such as aluminum chloride or ferric chloride.

38. The method of claim 36 in which cycliacylation is carried out with a dehydrating medium at a temperature from about 95°–115° C.

39. A method for preparing a compound of the formula

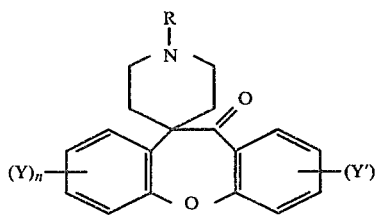

in which Y and Y' are the same or different and each can be hydrogen, chlorine, fluorine, bromine, methoxy, methylthio or trifluoromethyl; n and n' are the same or different and each can be an integer from 1 to 2, inclusive and R is loweralkanoyl or loweralkyl which comprises cycliacylating a compound of the formula

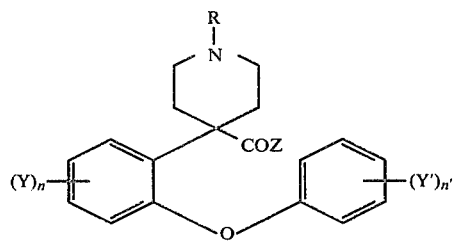

in which Z is OH or halogen under modified Friedel-Crafts conditions with a Lewis acid catalyst such as aluminum chloride or ferric chloride, a solvent such as methylene chloride and at a temperature ranging from about 15° C. to about 150° C.

40. A method for preparing a compound of the formula

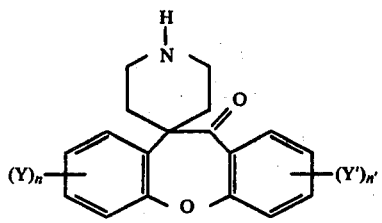

in which Y and Y' are the same or different and each can be hydrogen, chlorine, fluorine, bromine, methoxy, methylthio or trifluoromethyl, and n and n' are the same or different and each can be an integer from 1 to 2, inclusive, which comprises subjecting a compound of the formula

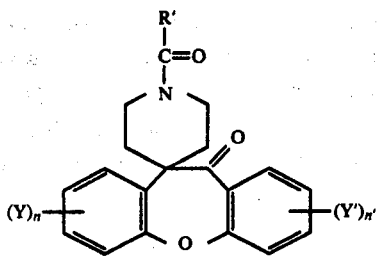

in which R' is loweralkyl to acid hydrolysis.

41. The method of claim 40 in which acid hydrolysis is carried out with 3 N hydrochloric acid under reflux conditions.

42. A method for preparing a compound of the formula

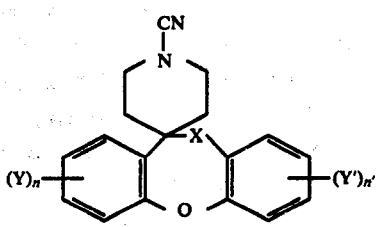

in which Y and Y' are the same or different and each can be hydrogen, chlorine, fluorine, bromine, methoxy, methylthio or trifluoromethyl; X is

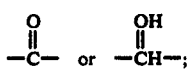

and n and n' are the same or different and each can be an integer from 1 to 2, inclusive, which comprises treating a compound of the formula

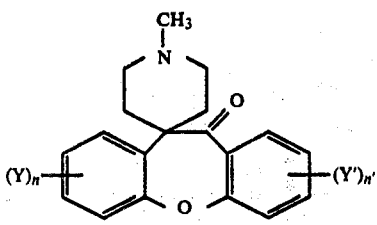

by the first step of the von Braun reaction.

43. A method for preparing a compound of the formula

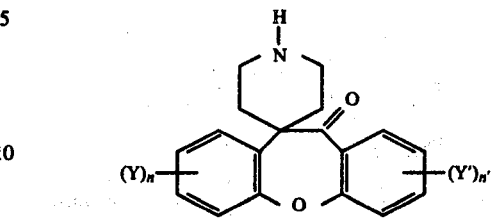

in which Y and Y' are the same or different and each can be hydrogen, chlorine, fluorine, bromine, methoxy, methylthio or trifluoromethyl and n and n' are the same or different and each can be an integer from 1 to 2, inclusive, which comprises subjecting a compound of the formula

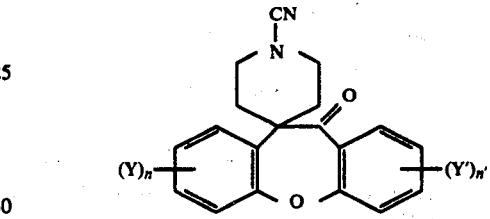

to hydrolysis according to the second step of the von Braun reaction.

44. The method of claim 43 in which a mixture of 3 N hydrochloric acid and glacial acetic acid (2:1) and a reaction temperature ranging from about 75° to about 150° C. are utilized.

45. A method for preparing a compound of the formula

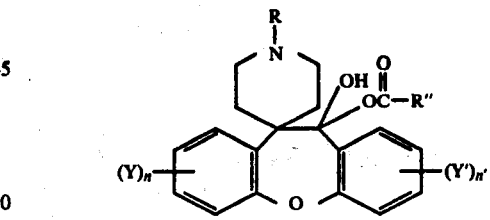

in which Y and Y' are the same or different and each can be hydrogen, chlorine, fluorine, bromine, methoxy, methylthio or trifluoromethyl; n and n' are the same or different and each can be an integer from 1 to 2, inclusive; R is

or CN; and R' and R" are the same or different and each is loweralkyl which comprises acylating under modified Friedel-Crafts conditions with a Lewis acid catalyst such as aluminum chloride or ferric chloride a compound of the formula

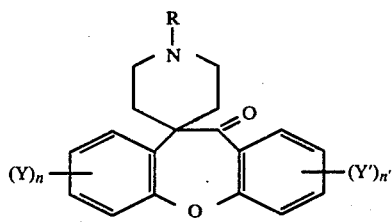

46. The method of claim 45 in which methylene chloride is the solvent and a reaction temperature ranging from about 15° to 150° C. is utilized.

47. A method for preparing a compound of the formula

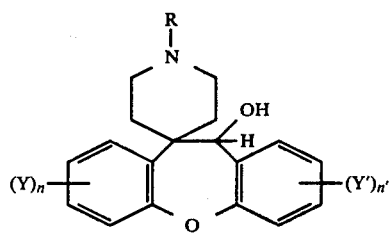

in which Y and Y' are the same or different and each can be hydrogen, chlorine, fluorine, bromine, methoxy, methylthio or trifluoromethyl; n and n' are the same or different and each can be an integer from 1 to 2, inclusive; R is H or loweralkyl; and R' is loweralkyl which comprises reducing a compound of the formula in which R=COR¹, CH₃ or CN

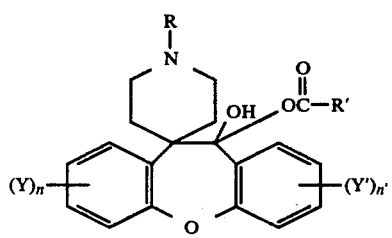

48. The method of claim 47 in which lithium aluminum hydride is the reducing agent, tetrahydrofuran is the solvent and a reaction temperature ranging from ambient to reflux of the reaction mixture are utilized.

49. A method for preparing a compound of the formula

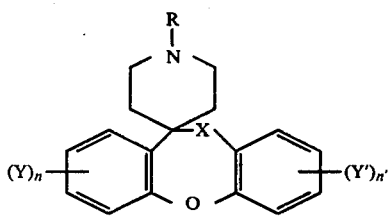

in which R is loweralkyl, hydroxyloweralkyl, loweralkynyl, loweralkenyl, phenylloweralkyl, phenoxyloweralkyl, cycloalkylloweralkyl, benzoylloweralkyl or

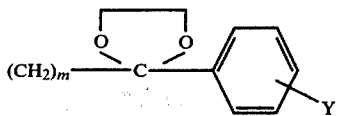

X is

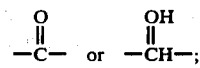

Y and Y' are the same or different and each can be hydrogen, chlorine, fluorine, bromine, methoxy, methylthio or trifluoromethyl; n and n' are the same or different and each can be an integer from 1 to 2, inclusive; and m is an integer from 1 to 4, inclusive, which comprises alkylating a compound of the formula

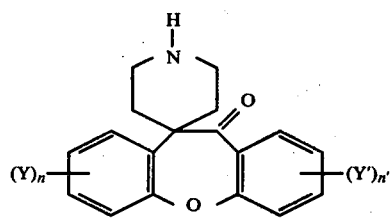

with an appropriate alkylating agent.

50. The method of claim 49 in which the alkylating agent is a compound of the formula R-hal and alkylation is carried out in a solvent such as dimethylformamide with an acid scavenger such as sodium bicarbonate or potassium bicarbonate and at a temperature ranging from about ambient to reflux.

51. The method of claim 50 further comprising the use of a reaction initiator such as potassium iodide.

52. A method for preparing a compound of the formula

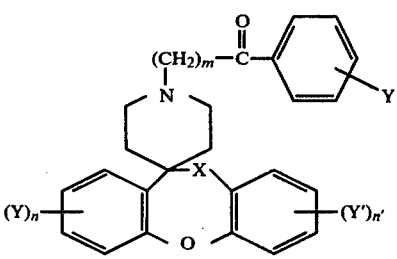

in which Y and Y' are the same or different and each can be hydrogen, chlorine, fluorine, bromine, methoxy, methylthio or trifluoromethyl; n and n' are the same or different and each can be an integer from 1 to 2, inclusive; and m is an integer from 1 to 4, inclusive, which comprises subjecting a compound of the formula

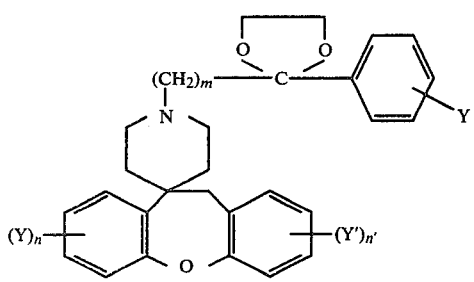

to acid hydrolysis.

53. The method of claim 52 in which the agent effecting hydrolysis is 3 N hydrochloric acid in ethyl alcohol.

54. A method for preparing a compound of the formula

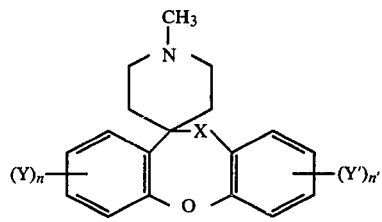

in which Y and Y' are the same or different and each can be hydrogen, chlorine, fluorine, bromine, methoxy, methylthio or trifluoromethyl; n and n' are the same or different and each can be an integer from 1 to 2, inclusive; and m is an integer from 1 to 4, inclusive, which comprises refluxing a compound of the formula

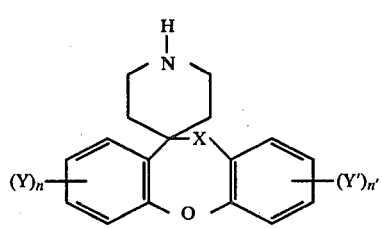

with formic acid and formaldehyde.

* * * * *

UNITED STATES PATENT AND TRADEMARK OFFICE
CERTIFICATE OF CORRECTION

PATENT NO. : 4,198,418
DATED : April 15, 1980
INVENTOR(S) : Helen H. Ong, James A. Profitt It is certified that error appears in the above-identified patent and that said Letters Patent are hereby corrected as shown below:

Column 1, line 37, change " 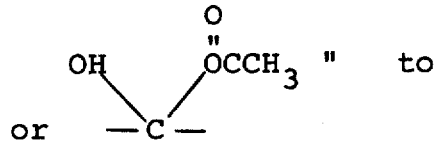 " to

-- or 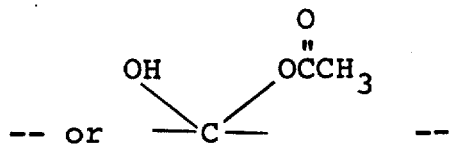 --

Column 9, line 66 and column 20, line 67, change
"...oxospiro-[dibenz..." to --...oxospiro[dibenz...--

Column 10, line 7, column 17, lines 13 and 44, change
"...[dibenz(b,f)-oxe..." to --...[dibenz(b,f)oxe...--

Column 10, line 41, change "...piro-[dibenz..." to
--...piro[dibenz...--

Column 10, line 48, column 14, line 48 and column 17, line 55,
change "...dibenz-(b,f)..." to --...dibenz(b,f)...--

Column 12, line 47 and column 13, line 7, change
"...phenyl)-piperidine" to --...phenyl)piperidine--

Column 17, line 40, change "...propyl)-spiro..." to
--...propyl)spiro--

Column 17, line 63, change "...piperidine]-ethylene" to
--...piperidine[ethylene--

UNITED STATES PATENT AND TRADEMARK OFFICE
CERTIFICATE OF CORRECTION

PATENT NO. : 4,198,418
DATED : April 15, 1980
INVENTOR(S) : Helen H. Ong, James A. Profitt It is certified that error appears in the above-identified patent and that said Letters Patent are hereby corrected as shown below:

Column 18, lines 38 and 39, change "total h" to --total hal--

Column 18, line 52, change "...propynyl)-spiro..." to
   --...propynyl)spiro...--

Column 19, line 62, change "alcohol-3 N" to --alcohol -3N--

Column 22, line 25, change "...benzoyl)-propyl]..." to
   --...benzoyl)propyl]...--

Column 23, line 45, change "...y)-benzyl" to --...y)benzyl--

Column 24, line 6, change "The is was slowly" to
   --The pH is slowly--

Column 24, line 41, change "alcoholether" to --alcohol-ether--

Column 25, line 33, change "...y)-phenyl]-..." to
   --...y)phenyl]-...--

UNITED STATES PATENT AND TRADEMARK OFFICE
CERTIFICATE OF CORRECTION

PATENT NO. : 4,198,418
DATED : April 15, 1980
INVENTOR(S) : Helen H. Ong, James A. Profitt It is certified that error appears in the above—identified patent and that said Letters Patent is hereby corrected as shown below:

Claim 24, change "...10,11- dihydro-..." to --...10,11-dihydro-...--.

Signed and Sealed this

Twenty-third Day of December 1980

[SEAL]

Attest:

SIDNEY A. DIAMOND

Attesting Officer

Commissioner of Patents and Trademarks